United States Patent [19]
Gray et al.

[11] Patent Number: 5,851,769
[45] Date of Patent: Dec. 22, 1998

[54] QUANTITATIVE DNA FIBER MAPPING

[75] Inventors: Joe W. Gray, San Francisco; Heinz-Ulrich G. Weier, Oakland, both of Calif.

[73] Assignee: The Regents of the University of California, Oakland, Calif.

[21] Appl. No.: 534,479

[22] Filed: Sep. 27, 1995

[51] Int. Cl.[6] .............................. C12Q 1/68; C12P 19/34
[52] U.S. Cl. .............................................. 435/6; 435/91.2
[58] Field of Search ........................ 435/6, 91.2; 935/77, 935/78

[56] References Cited

PUBLICATIONS

Collins, F. and Galas, D., "A New Five–Year Plan for the U.S. Human Genome Project," *Science* 262:43–46 (1993).
Mckusick, V.A., "Current trends in mapping human genes," *FASEB J.* 5:12–19 (1991).
Weissenbach, J., et al., "A second–generation linkage map of the human genome," *Nature* 359:794–801 (1992).
Wilkes, D., et al., "Identification of CpG Islands in a Physical Map Encompassing the Friedrech's Ataxia Locus," *Genomics* 9:90–95 (1991).
Cox, D.R., et al., "Radiation Hybrid Mapping: A Somatic Cell Genetic Method for Constructing High–Resolution Maps of Mammalian Chromosomes," *Science* 250:245–250 (1990).
Frazer, K.A., "A Radiation Hybrid Map of the Region on Human Chromosome 22 Containing the Neurofibromatosis Type 2 Locus," *Genomics* 14:574–584 (1992).
Boehnke, M., et al., "Statistical Methods for Multipoint Radiation Hybrid Mapping," *Am. J. Hum. Genet.* 49:1174–1188 (1991).
Burmeister, M., et al., A Map of the Distal Region of the Long Arm of Human Chromosome 21 Constructed by Radiation Hybrid Mapping and Pulsed–Field Gel Electrophoresis, *Genomics* 9:19–30 (1991).
Lichter, J.B., et al., "Physical and Genetic Maps for Chromosome 10," *Genomics* 16:320–324 (1993).
Trask, B., et al., "Fluorescence in Situ Hybridization Mapping of Human Chromosome 19: Cytogenetic Bank Location of 540 Cosmids and 70 Genes or DNA Markers," *Genomics* 15:133–145 (1993).
Müller, U. and Lalande, M., "A Physical Map of the Human Y–Chromosome Short Arm," *Genomics* 7:517–523 (1990).
Warrington, J.A. and Bengtsson, U., "High Resolution Physical Mapping of Human 5q31–q33 Using Three Methods: Radiation Hybrid Mapping, Interphase Fluorescence in Situ Hybridization, and Pulsed–Field Gel Electrophoresis," *Genomics* 24:395–398 (1994).
Schlessinger, D., "Yeast artificial chromosomes: tools for mapping and analysis of complex genomes," *Trends in Genetics* 6:248 and 255–258 (1990).
Albertsen, H.M., et al., "Construction and characterization of a yeast artificial chromosome library containing seven haploid human genome epuivalents," *Proc. Natl. Acad. Sci. USA* 87:4256–4260 (1990).
Bellanné–Chantelot, C., et al., "Mapping the Whole Human Genome by Fingerprinting Yeast Artificial Chromosomes," *Cell* 70:1059–1068 (1992).
Chumakov, I., et al., "Continuum of overlapping clones spanning the entire human chromosome 21q," *Nature* 359:380–387 (1992).
Cohen, D., et al., "A first–generation physical map of the human genome," *Nature* 366:698–701 (1993).

(List continued on next page.)

*Primary Examiner*—Eggerton A. Campbell
*Attorney, Agent, or Firm*—Medlen & Carroll, LLP

[57] ABSTRACT

The present invention relates generally to the DNA mapping and sequencing technologies. In particular, the present invention provides enhanced methods and compositions for the physical mapping and positional cloning of genomic DNA. The present invention also provides a useful analytical technique to directly map cloned DNA sequences onto individual stretched DNA molecules.

13 Claims, 9 Drawing Sheets

OTHER PUBLICATIONS

Olson, M.V., "The human genome project," *Proc. Natl. Acad. Sci. USA* 90:4338–4344 (1993).

Selleri, L., et al., "Detection and Characterization of Chimeric Yeast Artificial Chromosome Clones by Fluorescent in Situ Suppression Hybridization," *Genomics* 14:536–541 (1992).

Vetrie, D., et al., "Construction of a 5.2–Megabase Physical Map of the Human X Chromosome at Xq22 Using Pulsed–Field Gel Electrophoresis and Yeast Artificial Chromosomes," *Genomics* 15;631–642 (1993).

Brandriff, B.F., et al., "Order and Genomic Distances among Members of the Carcinoembryonic Antigen (CEA) Gene Family Determined by fluorescence in Situ Hybridization," *Genomics* 12:773–779 (1992).

Lu–Kuo, J.M., et al., "Construction of a YAC contig and a STS map spanning at least sven megabasepairs in chromosome 5q34–35," *Hum. Mol. Genet.* 3:99–106 (1994).

Kwiatkowski, T.J., et al., "Rapid identification of yeast artificial chromosome clones by matrix pooling and crude lysate PCR," *Nucl. Acids Res.* 18:7191–7192 (1990).

Westbrook, C.A., et al., "Physical and genetic map of 5q31: use of fluorescence in situ hybridization data to identify errors in the CEPH database," *Cytogenet. Cell Genet.* 67:86–93 (1994).

Green, E.D. and Olson, M.V., "Systematic screening of yeast artificial–chromosome libraries by use of the polymerase chain reaction," *Proc. Natl. Acad. Sci. USA* 87:1213–1217 (1990).

Coffey, A.J., et al., "Construction of a 2.6–Mb Contig in Yeast Artificial Chromosomes Spanning the Human Dystrophin Gene Using an STS–Based Approach," *Genomics* 12:474–484 (1992).

Nelson, D.L., "Current Methods for YAC Clone Characterization," *Genet. Analysis, Techniques and Appln.* 7:100–106 (1990).

Stucliffe, J.S., et al., "PCR amplification and Analysis of Yeast Artificial Chromosomes," *Genomics* 13:1303–1306 (1992).

Zucchi, I. and Schlessinger, D., "Distribution of Moderately Repetitive Sequences pTR5 and LF1 in Xq24–q28 Human DNA and Their Use in Assembling YAC Contigs," *Genomics* 12:264–275 (1992).

Porta, G., et al., "Alu and L1 Sequence Distributions in Xq24–q28 and Their Comparative Utility in YAC Contig Assembly and Verification," *Genomics* 16:417–425 (1993).

Stallings, R.L., et al., "Evaluation of a Cosmid Contig Physical Map of Human Chromosome 16," *Genomics* 13:1031–1039 (1992).

Tynan, K., et al., "Assembly and analysis of cosmid contigs in the CEA–gene family region of human chromosome 21," *Nucl. Acids Res.* 20:1629–1636 (1992).

Nižetić, D., et al., "An integrated YAC–overlap and 'cosmid–pocket' map of the human chromosome 21," *Hum. Mol. Genet.* 3:759–770 (1994).

Patil, N., et al., "A high resolution physical map of 2.5 Mbp of the Down syndrome region on chromosome 21," *Hum. Mol. Genet.* 3:1811–1817 (1994).

Pierce, J.C., et al., "A positive selection vector for cloning high molecular weight DNA by the bacteriophage P1 system: Improved cloning efficacy," *Proc. Natl. Acad. Sci. USA* 89:2056–2060 (1992).

Shizuya, H., et al., "Cloning and stable maintenance of 300–kilobase–pair fragments of human DNA in *Escherichia coli* using an F–factor–based vector," *Proc. Natl. Acad. Sci. USA* 89:8794–8797 (1992).

Chang, E., et al., "Generation of a Human Chromosome 18–specific YAC Clone Collection and Mapping of 55 Unique YACs by FISH and Fingerprinting," *Genomics* 17:393–402 (1993).

Branscomb, E., et al., "Optimizing Restriction Fragment Fingerprinting Methods for Ordering Large Genomic Libraries," *Genomics* 8:351–366 (1990).

Green, E.D. and Green, P., "Sequence–tagged Site (STS) Content Mapping of Human Chromosomes: Theoretical Considerations and Early Experiences," *PCR Meth. Appl.* 1:77–90 (1991).

Nelson, D.L., "Applications of polymerase chain reaction methods in genome mapping," *Curr. Op. Genet. Develop.* 1:62–68 (1991).

Hoheisel, J.D. and Lehrach, H., "Use of reference libraries and hybridisation fingerprinting for relational genome analysis," *FEBS Lett.* 325:118–122 (1993).

Green, E.D., et al., "Systematic Generation of Sequence–Tagged Sites for Physical Mapping of Human Chromosomes: Application to the Mapping of Human Chromosome 7 Using Yeast Artificial Chromosome," *Genomics* 11:548–564 (1991).

Arveiler, B., "Yeast Artificial Chromosome Recombinants in a Global Strategy for Chromosome Mapping," *Meth. Mol. Biol.* 29:403–423 (1994).

Trask, B., et al., "The Proximity of DNA Sequences in Interphase Cell Nuclei Is Correlated to Genomic Distance and Permits Ordering of Cosmids Spanning 250 Kilobase Pairs," *Genomics* 5:710–717 (1989).

Haaf, T. and Ward, D.C., "High resolution ordering of YAC contigs using extended chromatin and chromosomes," *Hum. Mol. Genet.* 3:629–633 (1994).

Heiskanen, M. et al., "High Resolution Mapping Using Fluorescence In Situ Hybridization to Extended DNA Fibers Prepared form Agarose–Embedded Cells," *BioTechniques* 17:928 (1994).

Kacian, D.L., et al., "A Replicating RNA Molecule Suitable for a Detailed Analysis of Extracellular Evolution and Replication," *Proc. Natl. Acad. Sci. USA* 69:3038–3042 (1972).

Chamberlin, M., et al., "New RNA Polymerase from *Escherichia coli* infected with Bacteriophage T7," *Nature* 228:227–231 (1970).

Wu, D.Y. and Wallace, R.B., "The Ligation Amplification Reaction (LAR)—Amplification of Specific DNA Sequences Using Sequential Rounds of Template–Dependent Ligation," *Genomics* 4:560–569 (1989).

*PCR Technology. Principles and Applications for DNA Amplification*, H.A. Erlich (ed.) (Stockton Press 1989).

Brandriff, B., et al., "A New System for High–Resolution DNA Sequence Mapping in Interphase Pronuclei," *Genomics* 10:75–82 (1991).

van den Engh, G., et al., "Estimating Genomic Distance from DNA Sequence Location in Cell Nuclei by a Random Walk Model," *Science* 257:1410–1412 (1992).

Wiegant, J., et al., "High–resolution in situ hybridization using DNA halo preparations," *Hum. Mol. Genet.* 1:587–591 (1992).

Lawrence, J.B., et al., "Extending the capabilities of interphase chromatin mapping," *Nature Genet.* 2:171–172 (1992).

Parra, I. and Windl, B., "High resolution visual mapping of stretched DNA by fluorescent hybridization," *Nature Genet.* 5:17–21 (1993).

Tocharoentanaphol, C., et al., "Multicolor fluorescence in situ hybridization on metaphase chromosomes and interphase Halo–preparations using cosmid and YAC clones for the simultaneous high resolution mapping of deletions in the dystrophin gene," *Hum. Genet.* 93:229–235 (1994).

Florijn, R.J., et al., "High–resolution DNA Fiber–FISH for genomic DNA mapping and colour bar–coding of large genes," *Human Mol. Genet.* 4:831–836 (1995).

Bensimon, A., et al., "Alignment and Sensitive Detection of DNA by a Moving Interface," *Science* 265:2096–2098 (1994).

Meltzer, P.S., et al., "Rapid generation of region specific probes by chromosome microdissection and their application," *Nature Genet.* 1:24–28 (1992).

Kallioniemi, A., et al., "Comparative Genomic Hybridization for Molecular Cytogenetic Analysis of Solid Tumors," *Science* 258:818–821 (1992).

Mascio, L.N., et al., Semiautomated DNA Probe Mapping Using Digital Imaging Microscopy: I. System Development, *Cytometry* 19:51–59 (1995).

Sakamoto, M., et al., "Semiautomated DNA Probe Mapping Using Digital Imaging Microscopy: II. System Performance," *Cytometry* 19:60–69 (1995).

Chu, B.C.F. and Orgel, L.E., "Ligation of oligonucleotides to nucleic acids or proteins via disulfide bonds," *Nucleic Acids Res.* 16:3671–3691 (1988).

Weetall, H.H., "Preparation of Immobilized Proteins Covalently Coupled Through Silane Coupling Agents to Inorganic Supports," *Appl. Biochem. Biotech.* 41:157–188 (1993).

Weier, H–U.G., et al., "Rapid Physical Mapping of the Human trk Protooncogene (NTRK1) to Human Chromosome 1q21–q22 by P1 Clone Selection, Fluorescenece in Situ Hybridization (FISH), and Computer–Assisted Microscopy," *Genomics* 26:390–393 (1995).

Reiter, R.E., et al., "Chromosome 17p Deletions and p53 Mutations in Renal Cell Carcinoma," *Cancer Res.* 53:3092–3097 (1993).

Sato, M., et al., "Ultraviolet–specific Mutations in p53 Gene in Skin Tumors in Xeroderma Pigmentosum Patients," *Cancer Res.* 53:2944–2946 (1993).

Kornberg, J.R. and Rykowski, M.C., "Human Genome Organization: Alu, Lines, and the Molecular Structure of Metaphase Chromosome Bands," *Cell* 53:391–400 (1988).

Matera, A.G., et al., "Recently Transposed Alu Repeats Result from Multiple Source Genes," *Nucleic Acids Res.* 18:6019–6023 (1990).

Shepard, N.S., et al., "Preparation and screening of an arrayed human genomic library generated with the P1 cloning system," *Proc. Natl. Acad. Sci. USA* 91:2629–2633 (1994).

Weier, H–U.G., et al., "Generation of Five High–Complexity Painting Probe Libraries from Flow–Sorted Mouse Chromosomes," *Genomics* 21:641–644 (1994).

Barker, D., et al., "A locus on Chromosome 11p with Multiple Restriction Site Polymorphisms," *Am. J. Hum. Genetics* 36:1159–1171 (1984).

Tanner, M.M., et al., "Increased Coy Number at 20q13 in Breast Cancer: Defining the Critical Region and Exclusion of Candidate Genes," *Cancer Res.* 54:4257–4260 (1994).

Strathman, M., et al., "Transposon–facilitated DNA sequencing," *Proc. Natl. Acad. Sci. USA* 88:1247–1250 (1991).

Lüdecke, H.J., et al., "Cloning defined regions of the human genome by microdissection of banded chromosomes and enzymatic amplification," *Nature* 338:348–350 (1989).

Lüdecke, H.J., et al., "Construction and characterization of band–specific DNA libraries," *Hum. Genet.* 84:512–516 (1990).

Telenius, H., et al., "Cytogenetic Analysis by Chromosome Painting Using DOP–PCR Amplified Flow–Sorted Chromosomes," *Genes, Chromosomes and Cancer* 4:257–263 (1992).

Weier, H–U.G., et al., "PCR cloning of a repeated DNA fragment from chinese hamster ovary (CHO) cell X chromosomes and mapping by fluorescence in situ hybridization," *DNA Sequence* 4:47–51 (1993).

Carter, N.P., "Cytogenetic Analysis by Chromosome Painting," *Cytometry* 18:2–10 (1994).

Kroisel, P.M., "PCR probes for chromosomal in situ hybridization of large–insert bacterial recombinants," *Cytogenetics and Cell Genetics* 65:97–100 (1994).

Weier, H–U.G., et al., "Synthesis of Y Chromosome–specific Labeled DNA Probes by In Vitro DNA Amplification," *J. Histochem. Cytochem.* 38:421–426 (1990).

Trautmann, U., et al., "Detection of APC region–specific signals by nonisotopic chromosomal in situ suppression (CISS)–hybridization using a microdissection library as a probe," *Hum. Genet.* 87:495–497 (1991).

Sambrook, J., et al., *Molecular Cloning: A Laboratory Manual*, Cold Spring Harbor Press, Cold Spring Harbor, pp. 9.16–9.23 (1989).

Weier, H–U. et al., "Generation of Highly Specific DNA Hybridization Probes for Chromosome Enumeration in Human Interphase Cell Nuclei: Isolation and Enzymatic Synthesis of Alpha Satellite DNA Probes for Chromosome 10 by Primer directed DNA Amplification," *Methods In Molec. Cell. Biol.*, 4:231–248 (1994).

Thundat, T., et al., "Atomic Force Microscopy of DNA on Mica and Chemically Modified Mica," *Scanning Microscopy*, 6(4): 911–918 (1992).

Puvion et al, Chromosoma 103(2):104–110, 1994.

Van Ommen et al, Curr Opin Genet Dev 5(3):304–308, 1995.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

TTCCTCTTCC TGCAGTACTC 20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GCCCCAGCTG CTCACCTACG 20

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CCTATCCTGA GTAGTGGTAA                                                                                                   20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCTTACCTCG CTTAGTGCTC                                                                                                   20

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AAAGCTCATC AGCGTGGTCG TG                                                                                                22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TGAGAGCCTT CAACCCAGTC AG                                                                                                22

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTAAAACGAC GGCCAGT                                                                                                      17

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AACAGCTATG ACCATG                                                                                                       16

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCCAAGCTTG CATGCGAATT CNNNNCAGG        29

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCCAAGCTTG CATGCGAATT C        21

QUANTITATIVE DNA FIBER MAPPING

FIELD OF THE INVENTION

The present invention relates generally to the field of DNA mapping and sequencing, and in particular to enhanced methods of physical mapping and positional cloning of genomic DNA.

BACKGROUND

One of the broad objectives of the Human Genome Project is the creation of high-resolution genetic and physical maps, and ultimately to determine the complete nucleotide sequence of the human genome. The ambitious goal of sequencing the entire human genome, comprising approximately 3 billion base pairs, presents one of the most formidable challenges of modern science. See, e.g., Collins and Galas, *Science* 262:43–6 (1993). The result of this initiative will be to localize the estimated 50,000–100,000 human genes and acquire information that will enable development of a better understanding of the relationship between genome structure and function. The identification of all the genes within the human genome will lead to the development of accurate diagnostics for most inherited diseases.

To achieve these goals, new methodologies that provide more rapid, efficient, and cost effective means of genome analysis will be required. Sequencing, although already under way for limited segments of the genome, will await further progress in gene mapping, and in particular, the creation of ordered maps of minimally overlapping clones (i.e., contig maps representing the minimal tiling path) for each chromosome in a form suitable for DNA sequencing [McKusick, *FASEB J.* 5:12 (1991)].

Several different types of maps are being produced. Physical maps fall into one of the three groups: molecular, cytogenetic and radiation fragmentation maps, while genetic or linkage maps are based on recombination frequency [Botstein, et al., al., *Am J. Hum. Genet.* 32:314 (1980)]. Detailed genetic maps have proved useful in positional cloning of disease genes such as cystic fibrosis, sickle cell and Tay-Sachs disease, fragile X syndrome and monotonic dystrophy and genetic maps are continuously refined by isolation of additional polymorphic or variable number of tandem repeat markers and sequence tagged sites (STSs). In 1992, Weissenbach and coworkers provided the Genome Database with the sequences of 808 CA-repeats amplifiable by use of the polymerase chain reaction (PCR) and distributed throughout the entire human genome [Weissenbach, et al., *Nature* 359:794 (1992)]. The majority (80%) of these loci showed heterozygosities greater than 70% and had an average spacing of approximately 5 centiMorgan (cM), that is approximately 1 marker every 5 megabasepairs (Mbp). Since then, the number of markers on the Genethon map has increased significantly placing more than 5000 $(CA)_n$-type markers on the genetic map.

The determination of the distance between and the ordering of genetic markers by studying marker segregation in large pedigrees [Botstein, et al., supra] is facing major restrictions: the markers have to be polymorphic and informative in the families studied, and recombination has to occur between marker to establish their order. Absence of recombination between markers near a disease locus, for example the Friedreich's Ataxia locus assigned to chromosome 9q13–21.1, prevents the resolution of gene/probe in this region, impeding strategies for gene isolation [Wilkes, et al., *Genomics* 9:90 (1991)].

Many of these problems can be circumvented by radiation fragmentation or radiation hybrid (RH) mapping [Cox, et al., *Science* 250:245 (1990)], which, once an appropriate radiation hybrid cell panel has been generated and characterized, can establish a relative order and distances even for non-polymorphic markers. In this procedure, a hybrid cell line containing a single human chromosome in a rodent cell background is subjected to a high dose of X-rays, which result in chromosomal fragmentation. The chromosomal fragments are then recovered by fusion to a rodent recipient cell line, which nonselectively retains some hamster and human chromosomal pieces from the donor cell line. The presence or absence of an STS in a hybrid cell clone can then rapidly be tested by use of the polymerase chain reaction (PCR) [Cox, *Genomics* 14:574 (1992)]. Markers near one another on the chromosome are likely to be maintained on the same DNA fragment or lost together in a particular hybrid cell line. Although many RH cell lines contain several pieces from the human chromosomes, it is nevertheless possible to use a statistical analysis of cosegregation of markers to construct a map of higher resolution than is possible by classical somatic cell genetic approaches [Cox (1992), supra and Boehnke, et al., *Am. J. Hum. Genet.* 49:1174 (1991)].

The genetic maps have been useful for mapping disease genes to chromosomal regions, but much higher resolution maps are needed for cloning genes and for genome organization studies [Burmeister, et al., *Genomics* 9:19 (1991)]. Since such high resolution physical maps are widely acknowledged as being indispensable for large-scale, cost-effective gene discovery, the construction of high resolution physical maps of the human genome and model organisms continues to be one of the major goals of the human genome project [Collins and Galas, *Science* 262:43 (1993)].

Cytogenetic maps, based on the positions of hybridization along a metaphase chromosome as detected by fluorescence in situ hybridization (FISH), use fractional length of the chromosomes as their measure [Lichter, et al., *Genomics* 16:320 (1993)]. However, FISH to metaphase chromosomes allows the localization and ordering of cloned DNA fragments to within a resolution of only a few-megabases [Trask, et al., *Genomics* 15:133 (1993)], and is therefore not suitable for high-resolution map assembly.

Currently, most molecular mapping is accomplished by contig assembly and ordering of genomic DNA restricting fragments by pulse field gel electrophoresis (PFGE) [Muller and Lalande, *Genomics* 7:517 (1990)]. The ordering of markers from very large genomic regions such as entire chromosomes or larger chromosomal bands by PFGE is complicated, because enzymatic restriction sometimes generates different fragments of similar size that are undistinguishable by PFGE. This problem has been partially solved by PFGE analysis of RHs [Burmeister, supra]. However, data generated by either PFGE or RH mapping does not always agree, and conflicting data regarding marker distance or order can not be resolved by these techniques [Warrington and Bengtsson, *Genomics* 24:395 (1994)].

The recent progress in cloning large, megabasepair size genomic DNA in yeast artificial chromosomes (YACs) [Schlessinger, *Trends in Genetics* 6:248 and 255 (1990); Albertsen, et al., *Proc. Natl. Acad. Sci. USA* 87:4256 (1990); Bellanné-Chantelot, et al., *Cell* 70:1059 (1992); Chumakov, et al., *Nature* 359:380 (1992); Cohen, et al., *Nature* 366:698 (1993); and Olson, *Proc. Natl. Acad. Sci. USA* 90:4338 (1993)] has made it possible to rapidly construct Mbp resolution physical maps based on overlapping YAC clones. FISH has proved indispensable for identification of non-chimeric YAC clones and physical mapping of individual YAC clones on metaphase chromosomes [Selleri, et al., Genomics 14:536 (1992)]. To generate physical maps with a resolution of 1 Mbp or better, the YAC clones are ordered by combining different complementing analytic techniques: PFGE [Vetrie, et al., *Genomics* 15:631 (1993)], FISH with interphase cell nuclei or metaphase spreads [Brandriff, et al., *Genomics* 12:773 (1992); Lu-Kuo, et al., *Hum. Mol. Genet.* 3:99 (1994); Kwiatkowski, et al., *Nucl. Acids Res.* 18:7191 (1990); and Westbrook, et al., *Cytogenet. Cell Genet.* 67:86 (1994)], sequence tagged site (STS) contents mapping [Green and Olson, *Proc. Natl. Acad. Sci. USA* 87:1213 (1990); Coffey, et al., *Genomics* 12:474 (1992); Chumakov, supra; and Weissenbach, supra] and/or DNA repeat fingerprinting [Nelson, *Genet. Analysis, Techniques and Appln.* 7:100 (1990); Bellanné-Chantelot, supra; Sutcliffe, et al., *Genomics* 13:1303 (1992); Zucchi and Schlessinger, *Genomics* 12:264 (1992); and Porta, et al., *Genomics* 16;417 (1993)].

The high resolution maps providing ordered sets of cloned DNA fragments at the 100,000 kb level of resolution are then assembled by mapping smaller DNA fragments onto the YAC contig and saturating the region of interest. In general, high resolution maps are comprised of overlapping cosmids [Stallings, et al., *Genomics* 13:1031 (1992); Tynan, et al., *Nucl. Acids Res.* 20:1629 (1992); Nizetic, et al., *Hum. Mol Genet.* 3:759 (1994); and Patil, et al., *Hum. Mol. Genet.* 3:1811 (1994)], P1 clones [Pierce, et al., *Proc. Natl. Acad. Sci. USA* 89:2056 (1992)], bacterial artificial chromosomes (BACs) [Shizuya, et al., *Proc. Natl. Acad. Sci. USA* 89:8794 (1992)] or DNA fragments cloned into other vectors that are amenable to direct sequencing. Assembly of these maps requires identification of cloned DNA sequences that contain overlapping regions of the genome. This has been accomplished by various forms of clone fingerprinting (e.g., by identification of common restriction fragment or inter-Alu PCR patterns [Chang, et al., *Genomics* 17:393 (1993); Patil, supra; Branscomb, et al., *Genomics* 8:351 (1990); Green and Green, *PCR Meth. Appl.* 1:77 (1991); and Nelson, *Curr. Op. Genet. Develop.* 1:62 (1991)], by hybridization to filter bound clone arrays [Hoheisel and Lehrach, *FEBS Lett.* 325:118 (1993) and Bellanné-Chantelot, supra] (e.g., by hybridization with inter-Alu PCR fragments to arrayed inter-Alu products from target clones) and by identification of overlapping sequence tagged sites [Green, et al. *Genomics* 11:548 (1991) and Arveiler, *Meth. Mol. Biol.* 29:403 (1994)]. These techniques are limited because they do not readily yield information about contig orientation, extent of overlap of contig elements or provide information about the extent of gaps in the maps.

Fluorescence in situ hybridization (FISH) provides additional important information for physical map assembly. For example, FISH to interphase nuclei allows probes to be ordered with several 100 kb resolution [Trask, et al., *Genomics* 5:710 (1989); Brandriff et al., supra; and Warrington and Bengtsson, supra] and FISH to preparations of decondensed nuclear [Haaf and Ward, *Hum. Mol. Genet.* 3:629 (1994)] or isolated cloned DNA [Heiskanen, et al., *BioTechniques* 17:928 (1994)] allows visualization of probe overlap and provides some information about the existence and size of gaps in the map. However, none of these techniques provides quantitative information about the extent of clone overlap or about the separation between elements in the map because the chromatin onto which clones are mapped is condensed to varying degrees from site to site in these preparations.

In order to provide sequence ready, high resolution physical maps containing minimally overlapping contigs, the art needs improved mapping techniques. Such improved techniques will facilitate the speed and reduce the cost with which the sequencing of the entire human genome will be achieved.

SUMMARY OF THE INVENTION

The present invention provides a composition comprising a uniformly stretched nucleic acid fiber having a sequence, wherein the nucleic acid fiber is immobilized to a solid support in a manner such that a probe containing sequences essentially complementary to the sequence of the immobilized nucleic acid fiber is capable of binding specifically to the nucleic acid fiber. This binding is conducted in a manner such that no substantial background is produced upon detection of the bound probe. It is contemplated that the nucleic acid fiber will comprise either double or single-stranded deoxyribonucleic acid fiber or ribonucleic acid fiber. It is also contemplated that the nucleic acid fiber is stretched to a dimension of approximately 2.3 kilobases per micrometer. It is further contemplated that the solid support comprise a glass support. In one embodiment, the glass support is treated with 3-aminopropyltriethoxysilane.

In another embodiment, the present invention comprises a method of treating a nucleic acid fiber which is immobilized to a solid support, comprising the steps of: providing a nucleic acid fiber having a sequence immobilized to a solid support, and one or more labeled probes containing sequences that are essentially complementary to the sequence of the immobilized nucleic acid fiber; reacting the immobilized nucleic acid fiber with the probes under conditions wherein the probes are capable of binding to essentially complementary sequences present on the nucleic acid fiber, and wherein no substantial background is produced; and detecting the presence of probes bound to the nucleic acid fiber.

It is contemplated that the nucleic acid fiber used in the method of the present invention is double-stranded or single-stranded deoxyribonucleic or ribonucleic acid fiber. In one embodiment of the present invention, it is contemplated that the nucleic acid fiber used in the method of the present invention be uniformly stretched to a dimension of approximately 2.3 kilobases per micrometer.

It is further contemplated that the solid support used in the method of the present invention comprises a glass support which may be treated with 3-aminopropyltriethoxysilane. It is also contemplated that the labeled probe comprises a probe containing a reporter molecule selected from the group comprising biotin and digoxigenin.

In one embodiment of the method, the detection step comprises reacting probe bound to the nucleic acid fiber with a detection reagent. It is contemplated that various detection reagents be used, including, but not limited to such compounds as those of the group comprising AMCA-avidin, FITC-avidin, and rhodamine-labeled anti-digoxigenin antibodies. In one embodiment of the method, the labeled probe comprises a probe containing a reporter molecule. It is contemplated that various reporter molecules will be used with the present invention, including, but not limited to rhodamine and fluorescein isothiocyanate.

The present invention also comprises a method for the stretching of a nucleic acid molecule, comprising the steps of: providing a first solid support treated with 3-aminopropyltriethoxysilane, a solution comprising a nucleic acid molecule, and a second solid support; placing an aliquot of the solution comprising said nucleic acid molecule onto the first solid support; placing the second solid support on top of the aliquot of the solution in a manner such that the solution is covered; and allowing the solution to dry, whereby the nucleic acid molecule is uniformly stretched to a dimension of approximately 2.3 kilobases per micrometer.

In one embodiment of this method of the present invention, the nucleic acid molecule comprises a linear nucleic acid molecule. In an alternative embodiment, the target nucleic acid comprises a circular nucleic acid molecule.

The inevntion is not limted by the force used to stretch the nucleic acid fibers. The invention is not limited by the nature of the force used to stretch nucleic acid fibers. Nucleic acid fibers (e.g., DNA fibers) which are attached via an end to a solid support may be stretch using a variety of forces. In a preferred embodiment, the hydrodynamic force of a receding air-liquid meniscus is used to stretch the fibers. However other mechanical forces may be employed including gravity flow, centrifugal force, the mechanical force generated by placing a coverslip over a drop containing nucleic acid fibers resting upon a treated solid support and mechanical force generate by the action of placing and then removing a coverslip from a drop containing nucleic acid fibers resting upon a treated solid support. Additionally, electrical forces may be used to stretch fibers which are attached via an end to a solid support.

The binding of probes to stretched nucleic acid fibers may but does not require a denaturation step in all cases. For example, in some instances it may be desirable to bind a single-stranded probe to a double stranded nucleic acid molecule; this binding may occur via the formation of a triple helix and thus denaturation of the double-stranded nucleic acid molecule is not required.

The stretched double-stranded fibers provided herein may be used to study the base composition along the fiber through the use of dyes which have base pair specificities (e.g., using Hoechst dye which binds preferentially to double-stranded regions which are A+T rich and/or using chromomycin $A_3$ which binds preferentially to double-stranded regions which are G+C rich).

The methods and compositions of the present invention may be applied for comparative genomic hybridization, deletion analysis, translocation detection, physical map assembly, and gap analysis.

DEFINITIONS

Figure 1:
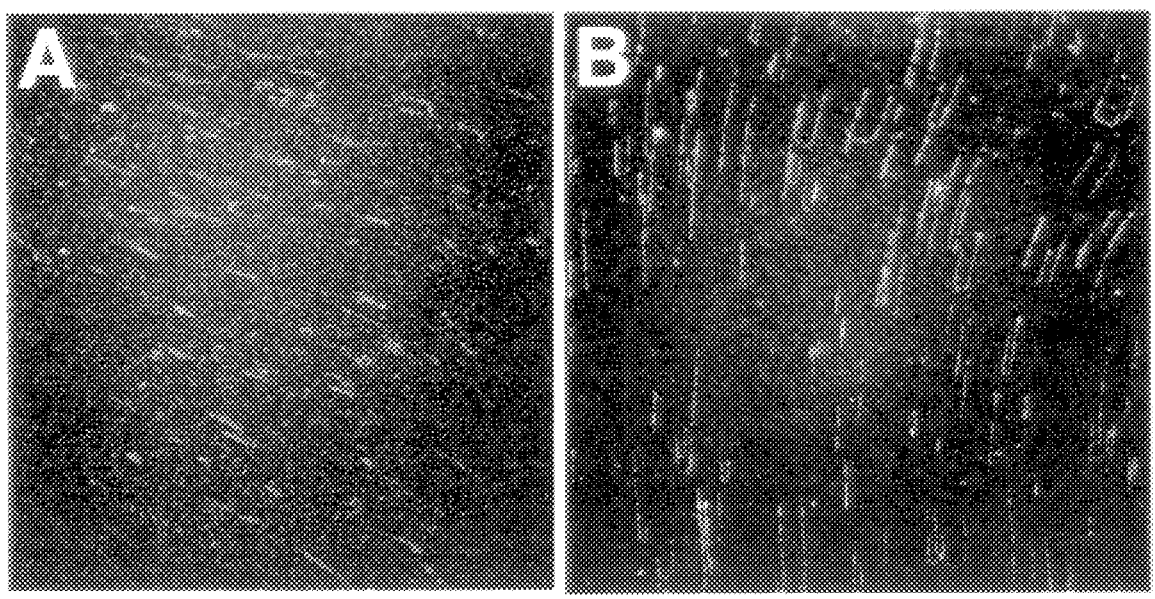
FIG. 1A shows a color image produced following hybridization and detection of fluorescently labeled HindIII restriction fragments to lambda DNA fibers stretched on a coverslip treated with vinyl-trichlorosilane.
FIG. 1B shows a color image produced following hybridization and detection of fluorescently labeled HindIII restriction fragments to lambda DNA fibers stretched on a coverslip treated with APS.

To facilitate understanding of the invention, a number of terms are defined below.

As used herein, the term "contig" refers to a group of clones which represent overlapping regions of a genome.

The term "contig map" as used herein means a map which depicts the relative order of a linked library of smaller overlapping clones along a larger clone or chromosomal segment.

The terms "sequence tagged sites" or "STS" refer to short (200–500 bp) DNA sequences that occur once in the human genome and whose location and nucleotide sequence are known. STSs provide landmarks along the physical map of the genome. "ESTs" refers to STSs derived from expressed genes (i.e., they are derived from cDNAs).

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," which provides a detectable signal in any detection system, including, but not limited to fluorescent, enzyme (e.g., ELISA, as well as enzyme-based histochemical assays), radioactive, and luminescent systems. It is not intended that the present invention be limited to any particular detection system or label. The probe may be labeled with non-isotopic labeling reagents such as biotin and digoxigenin; probes containing biotin may be detected using "detection reagents" such as avidin conjugated to any desirable label such as a fluorochrome. Probes containing digoxigenin may be detected using detection reagents such as antibodies directed against digoxigenin; these anti-digoxigenin antibodies may be labeled with any desirable label such as a fluorochrome. Alternatively, the probe may be directly labeled with a fluorochrome such as FITC or rhodamine; in such cases secondary detection reagents may not be required for the detection of the labeled probe.

The term "label" as used herein refers to any atom or molecule which can be used to provide a detectable (preferably quantifiable) "signal", and which can be attached to a nucleic acid or protein. Labels may provide "signals" detectable by fluorescence, radioactivity, colorimetry, gravimetry, X-ray diffraction or absorption, magnetism, enzymatic activity, and the like.

"Fluorescence in situ hybridization (FISH)" refers to a physical mapping technique which employs fluorescent tags to detect the hybridization of probes with metaphase chromosomes and with the less condensed somatic interphase chromatin. FISH is used herein for the hybridization of probes to stretched DNA fibers.

The terms "nucleic acid fiber" or "DNA fiber" refer to nucleic acid molecules, including DNA and RNA molecules which are substantially free of protein or other cellular components. In contrast, RNA and RNA molecules exist inside cells as protein/nucleic acid complexes. The removal of protein and other cellular components from DNA and RNA is achieved using techniques known to the art such as treatment of solutions comprising nucleic acids with proteinase K and/or extraction with phenol (phenol/chloroform/isoamyl alcohol or phenol/chloroform solutions may also be employed).

The present invention provides methods for the "uniform stretching" of DNA fibers. A "uniformly stretched" DNA fiber is a fiber which is stretched or extended to an equal degree over the length of the entire fiber. For example, the methods of the present invention stretch linear DNA fibers to approximately 2.3 kb/$\mu$m (in the absence of intercalating agents). The degree of stretching along the DNA fiber is shown herein to be independent of the length of the DNA fiber. It is noted that DNA fibers may be uniformly stretched to a lessor degree (to about 2.5 kb/$\mu$m) by employing solutions containing intercalating agents such as ethidium bromide, propidium iodide or acridine orange during the stretching process. It is desirable to reduce the amount of stretching (while maintaining uniformity of stretching) when very large DNA molecules are to be stretched as acquisition of images of molecules exceeding 470–500 kb in length becomes problematic [molecules of this size cannot be imaged in one frame using a set-up comprising 40×/1.4 N.A. lens, KP-1400 CCD chip]. Therefore, when the imaging of very large molecules is desired, intercalating agents may be employed to produce minimally elongated, straightened molecules. Alternatively, larger CCD camera chips may be employed to permit the acquisition of images of molecules up to 900 kb in a single frame.

The term "linear" when used in reference to a DNA molecule means that the DNA molecule exists as a single piece of DNA having two ends (if the DNA is a double-stranded DNA, then two double stranded ends are present). In contrast, a "circular" DNA molecule does not contain double-stranded ends; that is, the DNA exists as a circle. A double-stranded circular DNA may contain nicks (i.e., nicked circular DNA) which will result in the production of singe stranded ends. However the DNA molecule will remain in a circular rather than a linear form.

Nucleic acid molecules, such as DNA molecules, may be stretched out into a linear fiber. A process for the stretching of DNA molecules into linear fibers is referred to as "molecular combing." The process of "combing" employs the hydrodynamic force of a receding meniscus to stretch out a DNA fiber which is attached by an end to a solid support. The result of the combing process is a stretched DNA fiber. A DNA fiber which has been stretched using the hydrodynamic force of a receding meniscus may be referred to as a "combed" DNA fiber.

In order to stretch DNA molecules using the hydrodynamic force of a receding meniscus, the DNA molecule must be "attached" or "linked" or "immobilized" to a solid support via an end of the molecule. Attachment of DNA molecules via their ends to solid supports maybe achieved by placing the DNA molecule upon a solid support treated with a hetero-bifunctional agent having one functional group capable of forming linkages to the surface of the solid support and the other functional group is capable of binding to a nucleic acid molecule (e.g., DNA) via either a covalent or a non-covalent linkage.

The term "linkage" refers to the connection between two groups. For example, one functional group of the hetero-bifunctional agent is capable of binding or linking the hetero-bifunctional agent to a glass surface (possibly via SiOH groups present on the surface of the glass); the other functional group is capable of binding to or linking with a DNA molecule. The term linkage as used herein does not imply a covalent linkage; the linkage may be either covalent or non-covalent.

The terms "substantial background" or "high background" refers to the presence of undesirable signal (e.g., fluorescence) detected following in situ hybridization (e.g., FISH) of probes to DNA fibers stretched on treated solid supports (e.g., glass slides and coverslips) wherein the areas of signal (e.g., fluorescence) are observed scattered over the entire surface of the solid support (as opposed to signal which is localized to regions along the stretched DNA fiber). High levels of background may be due to the binding of the probe DNA directly to the treated glass surface or may be caused by excessive fragmentation of the DNA fiber during the stretching, denaturation, hybridization and/or washing steps. Fragments of the DNA fiber which move from their original position in the fiber to another position along the surface of the solid support can then bind the probe DNA (which is then followed by the binding of the detection reagents used when the probe is not directly labeled with a fluorochrome or other reporter molecule). Unacceptable (i.e., high or substantial) levels of background signal (e.g., fluorescence) in FISH experiments are those which preclude the detection or definition of the ends or boundaries of hybridized DNA fibers within 1–2 µm. A high background reduces the contrast between areas of alternating fluorochromes corresponding to differentially labeled probes along the hybridized DNA fiber (i.e., the boundary areas) and thus the definition of the boundary between the region of hybridization between two adjacent probes (or one probe and the underlying fiber) becomes difficult to assign. This leads to the definition of arbitrary boundaries during the interactive tracing of hybridized fibers which in turn reduces the accuracy of mapping.

"Interactive tracing" is a term known to the art and reflects the fact that an operator traces along an image of a hybridized fiber displayed on a computer screen to indicate the length to be measured by the computer. A computer program is then used to convert units measured by the computer as pixels into micrometers (see, the discussion of Image Analysis in the Detailed Description of the Preferred Embodiments below).

The term "background" when used in reference to the fluorescence observed after FISH of probes to stretched DNA fibers refers to signal fluorescence which is due to the presence of labeled probes at locations other than along the DNA fiber. In contrast, the solid support utilized maybe said to have a certain level of fluorescence due to the nature of the support itself. For example, glass may be used as a solid support because glass produced negligible levels of background fluorescence (due to fluorescence of the glass itself).

The term "specific binding" is used to indicate that a probe binds to or interacts with another complementary sequence (e.g., present on the DNA fiber) in a manner that is dependent upon the degree of complementarity of the two interacting sequences. In contrast "non-specific binding" occurs when a probe binds to another sequence in a manner which is independent of the degree of complementarity of the two interacting sequences. Specific binding does not require that two complementary sequences be completely complementary; the interact of two "essentially complementary" sequences is also said to comprise specific binding. Essentially complementary sequences are sequences which are "substantially homologous."

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization.

In addition, the art knows conditions which promote hybridization under conditions of high stringency (e.g., increasing the temperature of the hybridization and/or wash steps, the use of formamide in the hybridization solution, etc.). For example, conditions of high stringency as applied to FISH, comprise the use of a solution containing probes in 55% formamide (Gibco-BRL), 10% dextran sulfate, 100 ng/µl salmon sperm DNA in 2× SSC (300 mM NaCl, 30 mM Na citrate, pH 7.0) with a hybridization temperature of 37° C. Washing is then conducted using three changes of 2× SSC at 20° C. for 15 minutes per wash with slight agitation.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "vector" is used in reference to nucleic acid molecules that transfer DNA segment(s) from one cell to another. Vectors are used to introduce foreign DNA into host cells where it can be replicated (i.e., reproduced) in large quantities. The term "vehicle" is sometimes used interchangeably with "vector." Vectors, including "cloning vectors" allow the insertion of DNA fragments without the loss of the vector's capacity for self-replication. Cloning vectors may be derived from viruses, plasmids or genetic elements from eucaryotic and/or procaryotic organisms; vectors frequently comprise DNA segments from several sources. Examples of cloning vectors include plasmids, cosmids, lambda phage vectors, P1 vectors, yeast artificial chromosomes (YACs), bacterial artificial chromosomes (BACs) and P1-derived artificial chromosomes [PACs; Ioannou, et al., *Nature Genet.* 6:84 (1994)].

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "template," when used in reference to the polymerase chain reaction, refers to the region of nucleic acid bounded by the primers used for polymerase chain reaction. Thus, the "template" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a template sequence in a mixture of genomic DNA without cloning or purification. This process for amplifying the template sequence consists of introducing a large excess of two oligonucleotide primers to the DNA mixture containing the desired template sequence, followed by a precise sequence of thermal cycling in the presence of a DNA polymerase. The two primers are complementary to their respective strands of the double stranded template sequence. To effect amplification, the mixture is denatured and the primers then annealed to their complementary sequences within the template molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired template sequence. The length of the amplified segment of the desired template sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the template sequence become the predominant sequences (in terms of concentration) in the mixture, they are said to be "PCR amplified".

With PCR, it is possible to amplify a single copy of a specific template sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase [D. L. Kacian et al., *Proc. Natl. Acad. Sci USA* 69:3038 (1972)]. Other nucleic acid will not be replicated by this amplification enzyme. Similarly, in the case of T7 RNA polymerase, this amplification enzyme has a stringent specificity for its own promoters [M. Chamberlin et al., *Nature* 228:227 (1970)]. In the case of T4 DNA ligase, the enzyme will not ligate the two oligonucleotides where there is a mismatch between the oligonucleotide substrate and the template at the ligation junction [D. Y. Wu and R. B. Wallace, *Genomics* 4:560 (1989)]. Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences [*PCR Technology*, H. A. Erlich (ed.) (Stockton Press 1989)].

As used herein, the terms "PCR product", "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

GENERAL DESCRIPTION OF THE INVENTION

The assembly of sequence ready, high resolution physical maps and construction of minimally overlapping contigs for the human as well as model genomes requires accurate determination of the extent of overlap between adjacent clones as well as their relative orientation. This is presently done by procedures such as clone fingerprinting, southern blot analysis or clone end sequencing. These techniques are time consuming, labor intensive and sometimes produce ambiguous results.

In contrast, the present invention provides an analytical technique to directly map cloned DNA sequences onto individual stretched DNA molecules. This approach uses the hydrodynamic force of a receding meniscus to prepare straight high molecular weight DNA molecules that provide a linear template of ~2.3 kb/$\mu$m onto which the cloned probes can be mapped by in situ hybridization. This technique has numerous advantages over existing mapping techniques such as a very high density of mapping templates, reproducible stretching of the mapping template providing a linear genomic scale, determination of clone orientation and direct visualization of DNA repeats.

Of the various DNA mapping techniques currently available, fluorescence in situ hybridization (FISH) has proven to be very versatile because of its direct nature and sensitivity, its ability to visualize multiple targets in different colors simultaneously and its potential to cover a wide range of genomic resolutions. Fluorescence in situ hybridization provides additional information for physical map assembly. For example, FISH to metaphase chromosomes allows localization and ordering of cloned DNA fragments with few-megabase resolution [Lichter, et al., *Genomics* 16:320 (1993)] and FISH to interphase nuclei allows probes to be ordered with approximately 50 kb resolution [Brandriff, et al. *Genomics* 10:75 (1991) and van den Engh, et al., *Science* 257:1410 (1992)]. However, these techniques do not provide precise information about the extent of clone overlap or about the separation between elements in the map with high resolution.

This limitation has been partly removed using FISH with clones to be ordered to preparations of DNA fibers from decondensed nuclei [Wiegant, et al., *Hum. Mol. Genet.* 1:587 (1992); Lawrence, et al., *Nature Genet.* 2:171 (1992); Parra and Windl, *Nature Genet.* 5:17 (1993); Haaf and Ward, *Hum. Mol. Genet.* 3:629 (1994); Tocharoentanaphol, et al., *Hum. Genet.* 93:229 (1994)] and [Florijn et al., *Human Mol. Genet.* 4:831–36 (1995)] or isolated cloned DNA [Heiskanen, et al., supra]. These techniques allow visualization of probe overlap and provide semi-quantitative information about the existence and size of gaps in the map. However, the DNA in fiber preparations used to date have not been optimal for quantitative analysis because the fibers onto which clones are mapped are condensed to varying degrees and because useful DNA fibers have been hard to find.

In contrast to existing mapping methods which use DNA halo or other genomic DNA preparations, the present invention utilizes preparations of uniformly stretched DNA fibers. In comparison to the use of DNA halo or other genomic DNA preparations, the present invention provides several advantages. When linearized DNA molecules are used for mapping according to the methods of the present invention, the linearized DNA molecules are anchored to the solid substrate on one or sometimes both ends, thus providing a defined end of the mapping interval for each molecule prior to measurement. Mapping according to the methods of the present invention does not require a priori knowledge about the pattern of hybridization and, as described in detail herein for P1 and YAC fiber mapping, the presence of cloning vector-specific marker probes at one or both ends of the DNA fiber molecule allows discrimination between complete (i.e., full-length) and truncated molecules as well as determination of the orientation of the molecule (i.e., the insert). The methods of the invention, referred to as Quantitative DNA Fiber Mapping, enable absolute physical mapping of one or several cloned probes in the target genomic interval irrespective of their relative positions. Furthermore, information about the orientation of inserts and the location of probe overlap relative to the vector becomes readily available, when hybridizing cloned probes against each other.

In contrast, the DNA halo mapping technique described by Florijn et al., supra and other publications [Wiegant, et al., supra; Parra and Windl, supra; and Tocharoentanaphol, et al., supra] in which genomic DNA probes are mapped relative to each other and contig orientation, but not probe orientation is derived from the hybridization pattern. Information about the orientation of inserts in cloned probes, which is required for devising strategies for closure of gaps between contigs, cannot be obtained using DNA halo preps.

The present invention uses the hydrodynamic force of the receding meniscus to linearly stretch DNA molecules to the same extent, so that physical distanced (measured in $\mu$m) can be translated directly to genomic distances (measured in kb) and internal standards are not required. Thus, the DNA fiber mapping technique of the present invention is referred to as a "quantitative" method.

In contrast, the degree of DNA condensation in DNA halo preparations cannot be tightly controlled (Florijn, et al., supra list a factor of ~1.6), so that analysis requires the presence of probes of known size and normalization of hybridization track images.

In the methods of the present invention, suppression of DNA repeat sequence hybridization is not required since most interspersed repeats are physically separated by relatively large distances and can be visualized as hybridization domains along the stretched DNA fibers. This effect allows the mapping of DNA repeat sequences relative to other (single copy) sequences. However, if desired, repeat DNA hybridization can be suppressed by inclusion of unlabelled competitor DNA in the hybridization mix when performing the methods of the present invention.

In contrast, DNA halo, as well as any other genomic DNA preparation requires suppression hybridization for the mapping of probes containing DNA repeats.

The methods of the present invention allow the accurate mapping of probes which are part of gene families or regions duplicated in the genome. On the other hand, it is cumbersome, if not impossible, to map multi-copy probes to genomic (e.g., DNA halo) templates.

The methods of the present invention provide means for DNA fiber microdissection techniques due to the high density of labelled DNA target molecules in the absence of underlaying genomic DNA. DNA fiber microdissection is useful for the generation of probes in defined genomic intervals and the closure of gaps in contig maps.

While it may be possible to develop mechanical microdissection procedures for isolation of DNA fragments using DNA halo preparations, the presence of the large excess of genomic DNA would certainly complicate the isolation procedure. In contrast, quantitative DNA fiber mapping as described herein increases the concentration of target DNA by at least 3 orders of magnitude over genomic preparations. After molecular combing of YAC clones using the methods of the present invention, a 2 kb DNA fragment represents 0.2% of a 1 Mbp target interval, while the same 2 kb target amounts to little more than $0.66 \times 10^{-4}\%$ of genomic DNA preparations.

The non-uniform condensation of DNA fiber preparations can be minimized by employing molecular combing [Bensimon, et al., Science 265:2096 (1994)]. In this process, a solution of target DNA molecules onto which probes are to be mapped, is placed on a flat glass surface treated with vinyl-trichlorosilane so that the DNA molecules randomly attach at one or occasionally at both ends. The solution is then covered with a coverslip and allowed to dry. The DNA molecules are straightened and stretched at ambient temperature during drying by the hydrodynamic action of the receding meniscus. While Bensimon et al. teach a method for stretching individual DNA fibers, no methods are provided to give guidance for the use of these stretched fibers in FISH or other applications. As shown herein, the method of Bensimon et al., does not result in the preparation of stretched DNA fibers on a glass slide which is suitable for FISH due to unacceptably high levels of background fluorescence (discussed further below). Additionally, the lack of internal markers or probes by Bensimon et al., precludes conclusions about uniformity of stretching of DNA fibers using the disclosed method [Bensimon, et al., supra].

The present invention provides improved methods for the preparation of uniformly stretched DNA fibers and provides methods for the hybridization of labeled probes to these DNA fibers. As shown herein, the present invention provides methods which allow for the uniform stretching of DNA fibers; the stretching is shown to be uniform for DNA fibers ranging in size from 17 kb to over 1 Mbp (i.e., over 1000 kb). In particular, improved methods for the preparation of glass substrates are provided which allow FISH to the DNA fibers with low levels of background hybridization of labeled probes. In addition, improved methods for the manipulation of DNA solutions are provided which prevent the fragmentation or breakage of DNA fibers during the stretching procedure. Using the methods of the present invention, FISH and quantitative image analysis is used to map clones with few-kilobase resolution onto individual DNA molecules straightened by molecular combing thereby greatly facilitating physical map assembly. The reproducible DNA stretching and the high efficiency of DNA hybridization obtained in the present invention allows accurate mapping using only a few DNA fibers. These are easily found because combing results in a high density of linearized DNA fibers. Thus, only a few microscopic fields of view need to be examined.

The quantitative DNA fiber mapping technique of the present invention is highly useful as a tool for construction of kilobase resolution physical maps comprised of minimally overlapping cloned DNA sequences. The sizes of the clones (DNA sequences) can be assessed by direct measurement of their lengths after molecular combing or by measuring the extent of their hybridization domains along stretched DNA fibers. The degree of overlap between elements of a contig can be assessed by quantitatively mapping overlapping clones, one onto another, or by mapping these clones along DNA fibers representing larger genomic regions. The highly reproducible stretching achieved herein, which extends the DNA fibers to ~2.3 kb/$\mu$m, eliminates the need to scale each experiment using internal controls. On the other hand, hybridization experiments to determine the overlap between P1 clones, can include probes specific for the cloning vector sequences so that overlap can be immediately related to the orientation of the insert. Finally, clones can be mapped along YACs to determine order and to assess the extent of gaps between non-overlapping clones. This process is efficient since preparation of straight, uniformly stretched DNA fibers at high density is straightforward using molecular combing according to the methods of the present invention.

The high precision that can be achieved using quantitative DNA fiber mapping and the existence of extensive YAC contigs covering much of the human genome provide a simple strategy for assembly of "sequence ready" physical maps. The process begins with selection of clones homologous to an element of a YAC contig (e.g., by hybridization of the YAC to an array of DNA fragments cloned into cosmids, P1s, BACs, PACs or other vectors suitable as substrates for sequencing) or by subcloning the YAC. Each selected clone is then mapped onto the YAC using quantitative DNA fiber mapping. The end result of this process is a kilobase resolution map of the clones relative to each other, an estimate of the extent of overlap between them and an estimate of the sizes of gaps in the map. This information is then used to guide gap filling (a critical component of map assembly). Short gaps may be crossed by PCR or by selection of clones from small insert libraries while longer gaps might be filled by selection of additional large insert clones. The methods of the present invention permit the microdissection of DNA fibers and the preparation of probes by in vitro DNA amplification similar to the scheme applied for microdissection of metaphase chromosomes [Meltzer, et al., *Nature Genet.* 1:24 (1992)]. These methods provide further options for rapid gap closure as well as targeted generation of sequence tagged sites in the larger genomic interval defined by the high molecular weight DNA fiber.

Quantitative DNA fiber mapping can be performed in a high throughput, large scale format. Molecular combing has been conducted according to the methods of the present invention using twenty individual DNA samples per slides arranged in 4 rows×5 columns. The columns were separated by a thin border of rubber cement and DNA was dried under 5 mm wide strips cut from coverslips. The results showed clearly that clone overlap can be detection at this scale. The methods of the present invention therefore have major utility in the assembly of sequence ready physical maps.

The methods and compositions of the present invention provide rapid, and therefore cost-efficient, techniques which address the most critical issues in genome research, and in particular, the Human Genome Project. These issues include the assembly of high resolution physical maps for megabase size intervals, the closure of gaps between contigs, the generation of high density sequence tagged site (STS) maps for rapid walking in large insert genomic libraries and support of sequence assembly and quality control during the sequencing process (e.g., provide information about the relative position, size and chimerism status of sequencing templates). Significant cost savings is realized by the ability to produce contigs which represent the minimal tiling path for obtaining the sequence of a segment of the genome. Using existing methodology, the degree of redundancy in sequence large segments of the human genome is about 50%. The methods of the present invention will greatly reduce the degree of redundancy associated with sequencing the human genome.

The present invention provides improved methods and compositions which permit the rapid assembly of contig maps representing the minimal tiling path for a given segment of the genome and therefore will reduce the time and cost involved in obtaining the sequence of the human genome. The availability of the entire sequence of the human genome, or large portions thereof, provides a tremendous amount of information having great diagnostic value. In addition, the methods of the present invention provide methods which have direct diagnostic value. Quantitative DNA fiber mapping can be applied to the technique of comparative genomic hybridization to permit the rapid and precise localization of cytogenetic abnormalities associated with human tumors.

DETAILED DESCRIPTION OF THE PREFERRED EMBODIMENTS

The methods of the present invention, referred to as quantitative DNA fiber mapping, combines three techniques to permit the mapping of DNA fragments with a high degree of precision. These three techniques are: I. molecular combing, II. FISH and III. image analysis. Molecular combing allows the preparation of individual DNA molecules uniformly stretched to approximately 2.3 kb/$\mu$m. FISH is an analytical technique to visualize labeled DNA probes in the fluorescence microscope after binding to essentially complementary DNA molecules. The relative location of the bound probes is measured by digital image analysis techniques on images recorded from the fluorescence microscope.

I. Molecular Combing of DNA Fibers

The successful stretching of DNA fibers along a solid matrix requires that the DNA fibers bind preferentially at their respective 5' or 3' ends (or both) prior to the actual stretching process. The binding of the DNA to the glass surface must be sufficient to allow the DNA fiber to remain attached during the stretching process. However, the glass surface cannot be permitted to bind the DNA so tightly that the DNA fiber is firmly attached at multiple sites along its length prior to stretching. If the DNA binds too tightly to the surface, the passage of the receding water-air meniscus will not be sufficient to remove the DNA from the glass surface and therefore no stretching will occur. A balance must be struck such that the glass surface preferentially binds a portion of the DNA molecule (preferably at a single end of the molecule). The glass surface must also bind the target DNA to be stretched efficiently but must not promote the production of high levels of background.

A previous protocol for molecular combing employed glass surfaces treated with vinyl-trichlorosilane which produced vinyl end groups capable of binding to the ends of DNA fibers [Bensimon, et al., *Science* 265:2096 (1994)]. Bensimon et al. reported that the binding of DNA on silanized surfaces was dependent upon the pH, with efficient binding occurring at pH 5.5 but not at pH 8.0, and suggested that the presence of a free 5' phosphate group at the ends of the DNA molecule was required for the binding of the DNA molecules to the treated glass surface (unbound DNA molecules are swept by the receding interface).

In contrast, the present invention shows that the binding of DNA molecules to treated glass surfaces does not require a 5' phosphate group on the DNA molecule and that the binding is not dependent upon pH. Furthermore, the treatment of glass surfaces with vinyl-trichlorosilane was found to produce unacceptably high levels of background fluorescence.

In addition, a high percentage of DNA molecules were found to break or fragment during the combing process when 50 mM MES, pH 5.5 was employed for the suspension of the DNA. The present invention provides solutions which stabilize the DNA molecules during the combing process thereby preventing fragmentation of the DNA fiber. Additionally, the present invention employs silanation reagents which, in addition to producing superior results, are less toxic than the vinyl-trichlorosilane used by Bensimon et al, supra.

The present invention provides improved methods for the preparation of stretched DNA fibers. Solid supports (e.g., glass slides, glass cover slips) are treated with compounds comprising hetero-bifunctional groups wherein one functional group has the ability to form linkages to the surface of the solid support and the other functional group is capable of binding to a nucleic acid molecule (e.g., DNA) via either a covalent or a non-covalent linkage. The two functional groups are preferably separated by a hydrocarbon arm containing 3 to 12 carbon atoms. Desirable compounds are those which 1) allow the attachment of nucleic acid fibers in a manner that permits uniform stretching of the fiber, 2) do not promote a high background, 3) link the stretched nucleic acid fiber to the solid support in a manner that is not effected by the solutions and conditions used for denaturation, hybridization and detection of probes bound to the stretched nucleic acid fiber [e.g., the linkage must be resistant to the high temperatures used during denaturation (about 95°–100° C.), denaturation with compounds such as alcohol, photostable so that the linkage does not break during light microscopy and resistant to solutions containing solvents such as formamide] and 4) provide for the long-term (i.e., a minimum of 2–4 months) stability of the stretched DNA fibers when the surface containing the stretched fibers is stored at −20° C., 4° C. or at room temperature. As discussed in detail below, unacceptable levels of background fluorescence may be due to a variety of mechanisms including the binding of probe DNA directly to the treated glass surface or by excessive fragmentation of the DNA fiber during the stretching, denaturation, hybridization and/or washing steps followed by binding of the probe and any subsequent detection reagents. Unacceptable background levels exist when the background is so high that the boundary or the ends of the fiber cannot be detected within 1–2 $\mu$m.

While not limiting the invention to any particular mechanism by which linkage of nucleic acid molecules to a solid support is achieved such that the above functional characteristics are obtained, it is believed that compounds which form an attachment to the solid support via one functional group and which produce an exposed amine group (—NH$_2$) as the second functional group promote the binding of nucleic acid molecules to solid supports to produce the desired results. Hetero-bifunctional reagents capable of attaching to a solid support and capable of binding to the ends of nucleic acid molecules are found within the group of commercially available compounds comprising 3-aminopropyltriethoxysilane (APS; Sigma), 3-aminopropyltrimethoxy silane (Sigma), 3-aminopropyldiisopropylethoxysilane (Gelest), 3-aminopropyldimethylethoxysilane (Gelest) and 3-aminopropylmethyldiethoxysilane (Gelest).

In a preferred embodiment, standard microscope slides and coverslips are treated with 3-aminopropyltriethoxysilane (APS); this treatment permits the uniform stretching of DNA molecules during molecular combing and produces a solid surface comprising a stretched DNA which produces low levels of binding of probes to the treated surface during FISH (i.e., a low level of background is found following FISH).

The invention is not limited by the particular compound selected to treat the glass surface. Any compound capable of producing the desired results for the stretching of DNA fibers and FISH is suitable. In addition, the invention is not limited by the nature of the solid support utilized. Glass slides and coverslips may be employed; these supports are widely available and inexpensive and produce negligible levels of background fluorescence (due to fluorescence of the glass itself). Other solid supports such as sheets of mica are suitable. Mica provides a flatter surface compared to glass and the use of mica is preferred when atomic force microscopy is to be used for image analysis of hybridized nucleic acid fibers. Silicon nitride [100 Å thick squares or "windows" (1 mm×1 mm) are suitable] may be employed as the solid support when X-ray microscopy is to be conducted following FISH. The chosen solid support is treated as described below for the treatment of glass surfaces.

In a preferred embodiment, microscope slides are cleaned in equal parts of concentrated hydrochloric acid and methanol for at least 30 minutes followed by overnight immersion in 18M sulfuric acid. The slides are then washed in 8–10 changes of ultrapure water, immersed in boiling water for 10 minutes and air dried. Cleaned slides are placed in a 0.5–10% solution of 3-aminopropyltriethoxysilane (APS) in 95% ethanol for one hour, rinsed several times with water, washed with ethanol and air dried. Prior to use, slides are heated to 80°–110° C. for 60–120 min. or overnight. The use of lower APS concentrations requires shorter times at elevated temperature to produce substrates having similar DNA binding characteristics.

Glass (borosilicate) coverslips are cleaned and silanated in the same way as slides (above). The use of APS at concentrations above 2%, however, gives consistently excessive binding of the DNA at various points along the molecules so that the DNA molecules cannot not be stretched by the receding meniscus. Lowering the APS concentration to 0.5% and shortening the immersions times (to 1–2 min.) overcome this problem for the production of silanated coverslips.

For stretching of DNA fibers, a solution of target DNA molecules onto which probes are to be mapped is placed on the flat glass surface prepared so that the DNA molecules attach at one or occasionally at both ends. The DNA may be suspended in a buffer containing 1% p-phenylenediamine, 15 mM NaCl, 1 mM H$_2$PO$_4$, pH 8.0, 90% glycerol (AF-solution) to stabilize the DNA molecules during combing and reduce photobleaching during fluorescence microscopy. Other solutions, such as water, PBS, sodium borate buffer, MOPS buffer, MES buffer, TE buffer (pH 7.0–8.0), may be used for the suspension of the DNA.

The solution is covered with an untreated coverslip, the preparations are placed at 4° C. and allowed to dry. The coverslip is then removed, the slide is rinsed briefly with double-distilled water, air dried and stored at 4° C. Binding of DNA to the substrate and the stretching effect is monitored for each new batch of 20–30 slides or coverslips by fluorescence microscopy using DNA stained with YOYO-1 prior to deposition. This allows batches of slides that bind DNA too strongly to be rejected. Batches of slides or coverslips which bind the DNA so tightly that the DNA fiber does not appear to move or wiggle in solution are rejected.

The density of DNA molecules after molecular combing can be adjusted by altering the concentration of the DNA molecules prior to combing. Optimal results are obtained using DNA placed under 18 mm circular coverslips with either approximately 1×10$^6$ lambda DNA molecules of about 49 kb in size, or approximately 1×10$^5$ P1 molecules (about 97 kb) or about 3×10$^4$ YAC molecules of about 490 kb. Using these concentrations, on average one intact P1 or YAC DNA molecule with minimal overlap between individual DNA fibers is found every two fields of view.

The invention is not limited by the nature of the force used to stretch nucleic acid fibers. Nucleic acid fibers (e.g., DNA fibers) which are attached via an end to a solid support may be stretch using a variety of forces. In a preferred embodiment, the hydrodynamic force of a receding air-liquid meniscus is used to stretch the fibers. However other mechanical forces may be employed including gravity flow (i.e., the treated solid support is tilted or placed at an angle and a solution containing the nucleic acid fibers is placed on the support and allowed to flow downward), centrifugal force (i.e., the treated solid support is placed in a centrifuge using a suitable holder, the nucleic acid-containing solution is applied to the support and the support is then subjected to centrifugation using conditions which are sufficient to stretch the attached fiber). The mechanical force generated by placing a coverslip over a drop containing nucleic acid fibers resting upon a treated solid support can also be used to stretch the nucleic acid fibers. Additionally, the action of placing and then removing a coverslip from a drop containing nucleic acid fibers resting upon a treated solid support can be used to stretch the nucleic acid fibers. Because nucleic acid fibers are charged, electrical forces may be used to stretch fibers which are attached via an end to a solid support. Thus, it is clear that the invention is not limited by the nature of the force used to stretch nucleic acid fibers.

II. Fluorescence In Situ Hybridization (FISH)

Fluorescence in situ hybridization (FISH) of labeled probes to combed DNA fibers is used to permit physical mapping studies at high resolution.

Probes were prepared by labeling the DNA using random priming or in vitro DNA amplification using the polymerase chain reaction (PCR). Plasmid and P1 DNA for probe preparation was isolated by standard alkaline lysis procedures and YAC DNA was prepared from yeast clones using standard protocols [Sherman, et al., *Laboratory Course Manual for Methods in Yeast Genetics,* Cold Spring Harbor Laboratory Press, NY (1986)]. Probes can be labeled using a variety of haptens including haptens for non-isotopical labeling such as biotin, digoxigenin and fluorescein isothiocyanate (FITC). Probes are labeled with the haptens by incorporation of commercially available deoxynucleotide derivatives to which the haptens are bound covalently (e.g., fluorescein-dUTP, biotin-14-dCTP, digoxigenin-dUTP). The FITC-labeled probes can be seen in the fluorescence microscope by eye when bound in sufficient quantities or after immunocytochemical signal amplification using antibodies against FITC. The two indirect DNA labeling systems (biotin and digoxigenin) require post-hybridization detection of bound probe with affinity reagents (e.g., avidin, antibodies) carrying fluorochromes.

The quantitative DNA fiber mapping methods of the present invention are based on localization of bound DNA probes and measurement of the physical distance of the hybridization domain from either end of the stretched DNA molecule. Truncation of DNA molecules may lead to erroneous mapping results. To avoid this problem, probes that label only the flanking vector sequences were developed to allow the discrimination of whole from truncated molecules and to provide reference points for physical mapping. The vector part of fibers prepared from P1 and PAC clones [pAD10SacBII P1 vector (DuPont)], for example, can be counterstained by hybridization of a probe prepared from a recombinant (empty) P1 clone or by PCR-generated probes of about 1300–1400 bp in size derived from the P1 or PAC clone as described herein. Similarity, both YAC vector arms of clones from the CEPH YAC library (Centre d'Etudo du Polymorphisme Humain, Paris, France) can be counterstained by hybridizing a probe prepared from plasmid pYAC3.

The present invention provide both dual and triple probe labeling schemes. The triple label probe labeling scheme uses all three haptens (biotin, digoxigenin, FITC) to prepare a biotinylated probe that binds to the entire fiber, while probes to be mapped or that provide reference points are labeled with digoxigenin and FITC, respectively. The bound probes are detected after hybridization by incubation with AMCA-avidin (blue fluorescence), rhodamine-labeled sheep antibodies against digoxigenin (rhodamine-anti-digoxigenin; red fluorescence) and a mouse antibody against FITC followed by incubation with an FITC-conjugated horse-anti-mouse antibody (green fluorescence). The red (digoxigenin) signal is typically amplified by incubation of the slide (washed in three changes of 2× SSC) with a rhodamine-labeled rabbit-anti-sheep antibody. Visualization of the AMCA signal involves two signal amplification steps using a biotinylated goat-anti-avidin antibody followed by incubation with AMCA-avidin.

The dual label/dual color scheme involves the labeling of probe DNAs with biotin or digoxigenin and bound probes are detected with avidin-FITC and rhodamine-anti-digoxigenin. Hybridization signals are then amplified once with biotinylated goat-anti-avidin followed by a second layer of avidin-FITC and a Texas Red-labeled antibody against sheep IgG. The dual color scheme is used when the mapping of only one or two non-overlapping clones on to a larger DNA fiber is desired.

FISH analysis requires the DNA probe as well as the target to be single stranded for hybridization. An efficient protocol for denaturation/hybridization was the application of approximately 20 ng/$\mu$l of each probe in a solution containing 55% formamide, 10% dextran sulfate, 100 ng/$\mu$l salmon sperm DNA, 2× SSC to the slide, followed by the placement of a non-silanated coverslip on top. The combed DNA and probe(s) were then simultaneously denatured by incubation at 95°–100° C. for 3 minutes on a hot plate. The hybridizations were allowed to proceed overnight at 37° C. and the slides were then washed in 3 changes of 2× SSC at 20° C. for 15 minutes per wash. Bound probes were detected by conjugation with fluorochrome-labeled avidin and antibodies as describe above. Final washes of slides were done in two changes of 2× SSC, before they were mounted in antifade (AF)-solution for microscopic inspection.

III. Image Analysis

A computer-assisted fluorescence microscope was used for multi-color visualization of DNA molecules after FISH. The system consists of a Zeiss research microscope equipped with a cooled CCD camera (Photometrics), a computer controlled filter wheel, and a SUN workstation that controls the filters and cooled CCD camera [Kallioniemi, et al., *Science* 258:818 (1992)].

The essential optical feature of the microscope is the use of a multi-band beam splitter and emission filter, and a computer-controlled filter wheel to change the excitation filters. Each fluorochrome in the specimen is excited by selecting the appropriate excitation filter. The band passes in the beam splitter and emission filter are such that all of the fluorochrome-specific images can be obtained without moving any elements in the imaging pathway. The registration shifts between the red and green images are less that 0.1 $\mu$m (referred to the object) at all points in the digital image [Mascio, et al., *Cytometry* 19:51 (1995)]. The current filters are capable of excitation in single bands centered around 360 nm, 405 nm, 490 nm, and 560 nm, and visualization simultaneously in multiple bands in the vicinities of 450 nm (blue), 520 nm (green), and 600 nm (red). In addition, dual band excitation filters for simultaneous observation of FITC/Texas red were employed [Sakamoto, et al., *Cytometry* 19:60 (1995)].

The accuracy of quantitative DNA fiber mapping was initially assessed by measuring the location of hybridization signal of lambda DNA/Hind III restriction fragments hybridized on stretched lambda DNA molecules (Example 2). The 9.4 kb and 23 kb probes were labeled with biotin and the 4.3 kb and 6.6 kb probes were labeled with digoxigenin The hybridized probes were then detected with avidin-FITC and rhodamine-labeled anti-digoxigenin. The hybridization efficiency was uniformly high and most molecules showed alternating red and green fluorescing domains in the regions homologous to the probes as expected. The intact fibers were ~21.6 µm in length indicating that the 48.9 kb molecules were stretched to 2.26 kb/µm.

Forty-five molecules of approximately full length were selected for analysis. The longitudinal fiber axis was traced interactively and a computer program was used to calculate integrated fluorescence for 9 pixel wide cross-sections equivalent to 1.0 µm along the selected path. Map positions were determined by first calculating the ends of the linear molecules (10% of its peak value). The positions where the fluorescence of the 4.3 kb, 9.4 kb and 6.6 kb fragments had reached 50% of their value were used to define the boundaries of the labeled fragments. The difference between the measured boundaries and exact position of HindIII restriction sites was defined as the accuracy of the measurement. The interval between the 10% and 90% values was defined as mapping precision. The measured mean distances of the boundaries of the 4.3 kb, 6.6 kb and 9.4 kb HindIII fragments from the phage molecule endpoints were within approximately 2 kb of the known distances and the mapping precision was better than 3 kb for all measurements. The same algorithm was applied in initial studies where P1 molecules were mapped onto stretched YAC DNA fibers.

An even simpler scheme for mapping of plasmid clones on P1 DNA fibers was developed: the recorded images were converted to 24-bit tiff images, transferred from the SUN workstation to an Apple Macintosh computer and analyzed using routines of 'NIH Image V1.57'. This software allows one to interactively trace DNA fibers by drawing a segmented line and then the program calculates the length of the line in pixels. The pixel spacing was known from the microscope objective used in the experiment (63× magnification for molecules up to 100 kb, 40× magnification for all larger molecules) and was converted directly into µm (or kb using a factor of 2.3 kb/µm). Several distances along the hybridized fibers were measured in triplicate. On images recorded from P1 fibers, the total length of the fiber, the size of its vector part, the size of probe hybridization domains as well as distances from either end were measured. Measurement of all these distances may not be necessary in routine applications of quantitative DNA fiber mapping.

The output of NIH Image program provides the measurements in form of a list. This list was imported in to Microsoft Excel, reformatted manually and used to calculate average values for each fiber. The average values of several fibers were used to calculate mean values and standard deviations for fibers measured in one experiment. Relative standard deviations (C.V.s) were typically in the order of 5% of the measured value. Higher C.V.s provided a simple mean to control the analysis procedure; a high C.V. prompts a check of the data analysis results for operator errors and unusual or undesired images such as broken molecules or insufficiently stretched fibers.

EXPERIMENTAL

The following examples serve to illustrate certain preferred embodiments and aspects of the present invention and are not to be construed as limiting the scope thereof.

In the experimental disclosure which follows, the following abbreviations apply: CCD (charge coupled device); DAPI (4', 6-diamiidino-2-phenylindole); eq (equivalents); FITC (fluorescein isothiocyanate); M (Molar); µM (micromolar); N (Normal); mol (moles); mmol (millimoles); µmol (micromoles); nmol (nanomoles); gm (grams); mg (milligrams); µg (micrograms); ng (nanogram); L (liters); ml (milliliters); µl (microliters); cm (centimeters); mm (millimeters); µm (micrometers); nm (nanometers); °C. (degrees Centigrade); PBS (phosphate buffered saline); SDS (sodium dodecylsulfate); Tris-HCl (tris[Hydroxymethyl] aminomethanehydrochloride); rpm (revolutions per minute); YOYO-1 (YO-YO-1 iodide); LMP (low-melting point); DNA (deoxyribonucleic acid); RNA (ribonucleic acid); EDTA (ethylenediaminetetracetic acid); dATP (2'-deoxyadenosine 5'-triphosphate); dCTP (2'-deoxycytidinine 5'-triphosphate); dUTP (2'-deoxyuridine 5'-triphosphate); dNTP (2'-deoxyribonucleotide 5'-triphosphate); MES (2-[N-Morpholino]ethanesulfonic acid; MOPS (3-[N-Morpholino] propanesulfonic acid; American Scientific (American Scientific Products, McGraw Park, Ill.); ATCC (American Type Culture Collection, Rockville, Md.); BioRad (BioRad Laboratories, Inc., Hercules, Calif.); BM (Boehringer Mannheim, Indianapolis, Ind.); Chase (Chase Instruments Corp., Norcross, Ga.); Chroma Technology (Chroma Technology, Brattleboro, Vt.); DAKO (DAKOPATTS, Carpintera, Calif.); Difco (Difco Laborartories, Detroit, Mich.); duPont (E. I. DuPont de Nemours & Co.); Fischer (Fischer Scientific, Pittsburg, Pa.); Gelest (Gelest, Inc., Tullytown, Pa.); Gibco-BRL (Gibco-BRL Life Technologies, Inc., Gaithersburg, Md.); Hoefer (Hoefer, a division of Pharamica Biotech, Inc., Piscataway, N.J.); ICN (ICN Biochemicals, Costa Mesa, Calif.); Invitrogen (Invitrogen Corp., San Diego, Calif.); Molecular Probes (Molecular Probes, Eugene, Oreg.); NEB (New England Biolabs, Beverly, Mass.); Sigma (Sigma Chemical Co., St. Louis, Mo.); Stratagene (Stratagene Cloning Systems, LaJolla, Calif.); US Biochemical (US Biochemical Corp., Cleveland, Ohio); Vector (Vector Laboratories, Burlingame, Calif.); and Zeiss (Carl Zeiss, Inc., Thornwood, N.Y.).

Unless otherwise noted, all restriction enzymes were obtained from Boehringer Mannheim and restriction digests were performed according to the manufacturer's instructions.

The following reagents were obtained from Vector: Texas red anti-sheep IgG (H&L); fluorescein anti-mouse IgG (H&L); AMCA avidin D; biotinylated anti-avidin D; and fluorescein avidin DCS. Anti-digoxigenin-rhodamine, Fab fragments and Anti-digoxigenin-fluorescein, Fab fragments were obtained from BM.

Sequence alignments were conducted as follows. Alignment of the sequences of the pAD10SacBII cloning vector (DuPont; GenBank accession number U09128) and pWE15 cosmid vector (ATCC 37503; GenBank accession X65279) using MacVector (Kodak, New Haven, Conn.). A homology search using the daily update of the Genome Sequence Database (GSDB-LANL) was used to identify a 493 bp region of pWE15 with 100% (491/493) homology ending 46 bp upstream of the NotI site in pAD10SacBII. The sequence of the human p53 gene can be found at GenBank accession number X54156; analysis of this sequence reveals several clusters of Alu-type repeats.

AHC medium contains per liter: 1.7 g yeast nitrogen base, without amino acids and without ammonium sulfate (Difco); 5 g ammonium sulfate; 10 g acid casein hydrolysate (US Biochemical); 50 ml of 40% glucose (2% final); and 20 ml of 2 mg/ml adenine hemisulfate (40 µg/ml final). For solid medium, agar (20 g/l) is added to AHC medium.

Yeast cells containing specific nutritional markers were grown on SC medium lacking one or more amino acids. SC medium lacking a particular amino acid is referred to as "dropout" media. SC medium is made using the following components:

10× YNB (67 g yeast nitrogen base without amino acids in 1 liter water, filter-sterilized and stored in the dark).

Dropout mixture components

| adenine | 800 mg | arginine | 800 mg |
|---|---|---|---|
| aspartic acid | 4000 mg | histidine | 800 mg |
| leucine | 2400 mg | lysine | 1200 mg |
| methionine | 800 mg | phenylalanine | 2000 mg |
| threonine | 8000 mg | tryptophan | 800 mg |
| tyrosine | 1200 mg | uracil | 800 mg |

To make a dropout mixture, the above components are weighed out, leaving out the amino acid(s) to be selected for, combined, and ground into a fine powder using a mortar and pestle. SC dropout media (Ura-/Tryp-) is made by omitting uracil and tryptophan from the above components.

EXAMPLE 1

Quantitative DNA Fiber Mapping Using Large DNA Fragments

In order to develop methods which permit the mapping of clones with a few kilobase resolution onto individual DNA molecules straightened by molecular combing, the following experiments were conducted. First, the effect of pH on the binding of DNA fibers to glass surfaces was examined. Second, the requirement for a 5' phosphate group on the DNA fiber for molecular combing was examined. Third the effect of the use of various modified glass surfaces upon molecular combing and subsequent FISH was examined.

a) The Effect of pH on the Molecular Combing of DNA Fibers

The efficiency of binding linear DNA molecules to silanated glass surfaces in solutions having a pH varying from 5.5 to 9.6 was examined. Glass coverslips (18 mm, round) treated with vinyl-trichlorosilane were obtained from Dr. A. Bensimon (Laboratorie de Biophysique de l'ADN, Institut Pasteur, Paris, France); treatment of the coverslips was conducted as described in Bensimon et al., supra. A stock solution of lambda phage DNA (Sigma) was prepared at a concentration of $3.1 \times 10^9$ DNA molecules per microliter in water. The stock solution was the diluted 1:310 in to the following test solutions: water (pH 6.0), 50 mM MES, pH 5.5 50 mM MOPS, pH 5.5, TE buffer (10 mM Tris-HCl, pH 8.0; 1 mM EDTA), 1× PBS, pH 7.2 (Gibco-BRL) and 50 mM sodium borate, pH 9.6. One microliter of solutions containing $1 \times 10^7$ lambda molecules/μl in the above test solutions were then mixed with 1 μl of YOYO-1 (1 μM in $H_2O$, 0.001% DMSO) and 8 μl of the appropriate test solution (i.e., MES, MOPS, TE, water, etc.). Two to three microliters of each mixture was then placed onto the silanated coverslips. Untreated coverslips were placed on top of the drops and the binding of the DNA in the test solutions to the treated glass surface was examined by fluorescence microscopy. The extent of binding was assessed by observation of the DNA molecules; attachment of DNA molecules by a single end produced a molecule which rotated freely in solution about the fixed end. Successfully bound molecules remained attached to the glass slide and were stretched in a linear fashion as the air-water meniscus receded during drying.

Unexpectedly, the pH of the solution used for suspension of the DNA had no effect upon the efficiency of binding of the DNA molecules to the treated glass surface. All solutions tested resulted in the binding of approximately the same percentage of lambda DNA molecules.

It was found that suspension of DNA in water or any of the buffers examined above resulted in substantial DNA fragmentation during combing and that the resulting DNA fragments then coupled to the slide. The problem of DNA fragmentation was controlled by use of AF-solution (as described below in section c).

b) 5' Phosphate Groups Are Not Required for Molecular Combing

In order to determine whether the binding of DNA via the ends to treated glass surfaces was mediated by the interaction of the 5' phosphate and the vinyl group created by silanation of glass with vinyl-trichlorosilane, the following experiments were conducted. The 5' ends of lambda DNA were modified by reaction with cystamine (Pierce, Rockford, Ill.) (leaves a reactive 5'-amine) [Chu and Orgel, Nucleic Acids Res. 16:3671 (1988)] or subsequent reduction with dithiothreitol (results in production of 5'-sulfhydryl groups). The modified DNAs were then stained with YOYO-1 as described in section a) above. The stained DNAs were then placed on the vinyl-trichlorosilane-treated coverslips. The binding of the modified DNAs to the treated glass surface was examined by fluorescence microscopy as described above. Unexpectedly, the modification of the 5' phosphate group at the ends of the lambda DNA had no effect upon the ability of the DNA to bind to the silanated glass surface. In addition, activation of the glass substrate with glutaraldehyde or sulfosuccinimidyl 6-(3-[2-pyridyldithio] propionamido) hexanoate (SPDP) [Weetall, Appl. Biochem. Biotech. 41:157 (1993)] had little or no effect on DNA binding to the glass substrate. Theses results show that coupling of the DNA to the solid support may be mediated by groups other than the 5'-phosphate (i.e., the presence of a 5'-phosphate is not required for binding).

c) Comparison of the Effect of Various Treatments of Glass Surfaces Upon Molecular Combing Standard glass microscope slides and borosilicate coverslips were obtained from American Scientific, Fischer or Chase Instruments. Glass slides were cleaned in equal parts of concentrated hydrochloric acid and methanol for at least 30 minutes followed by overnight immersion in 18M sulfuric acid. The slides were then washed in 8–10 changes of ultrapure water, immersed in boiling water for 10 min. and air dried. Cleaned slides were placed in either 1) a 10% solution of (γ-glycidoxypropyl) trimethoxy silane (Hüls, America, Inc., Bristol, Pa.) in 95% ethanol or 2) a 10% solution of 3-aminopropyltriethoxy silane (APS, Sigma) in 95% ethanol. The slides were then treated in the desired solution at 20° C. for two [(γ-glycidoxypropyl) trimethoxy silane] or four hours (APS), rinsed three times with water, washed with ethanol and air dried. Prior to use, APS-treated slides were heated to 80°–110° C. overnight. The treatment of glass with APS results in the exposure of amino-groups while treatment with (γ-glycidoxypropyl) trimethoxy silane results in the exposure of epoxy groups. Glass substrates having either amino-, epoxy- or vinyl-groups (obtained from A. Bensimon) were compared for their suitability for the stretching of DNA fibers.

A solution comprising YOYO-1 stained lambda DNA in 50 mM sodium borate buffer, pH 9.6 was prepared as described in section a). Two to four microliters of the DNA mixture was then placed onto the silanated coverslip (vinyltrichlorosilane) or treated slides (epoxy- or amino-silane). The binding of DNA to the different surfaces was assessed initially by observing under a fluorescence microscope whether the DNA bound by the ends only or along the entire length of the DNA. It was found that the epoxy-derivatized slide bound the DNA too tightly; that is the DNA was bound along its entire length to the glass surface and therefore there was no portion of the DNA molecule freely moving in solution and available for stretching. The vinyl- and amino-derivatized glass surfaces were found to bind the DNA fibers by their ends and were then further examined for suitability for use in FISH experiments as follows.

Lambda DNA was stained with YOYO-1 as described above and 2–4 µl of the stained DNA in water was placed on either a vinyl-derivatized coverslip (vinyl-trichlorosilane) or an amino-derivatized slide (APS). The drops were then covered using untreated coverslips and the solution was allowed to dry to permit stretching of the DNA. The dried, stretched DNA fibers were then hybridized with labeled restriction fragments prepared by digestion of lambda DNA with HindIII.

Figure 2:
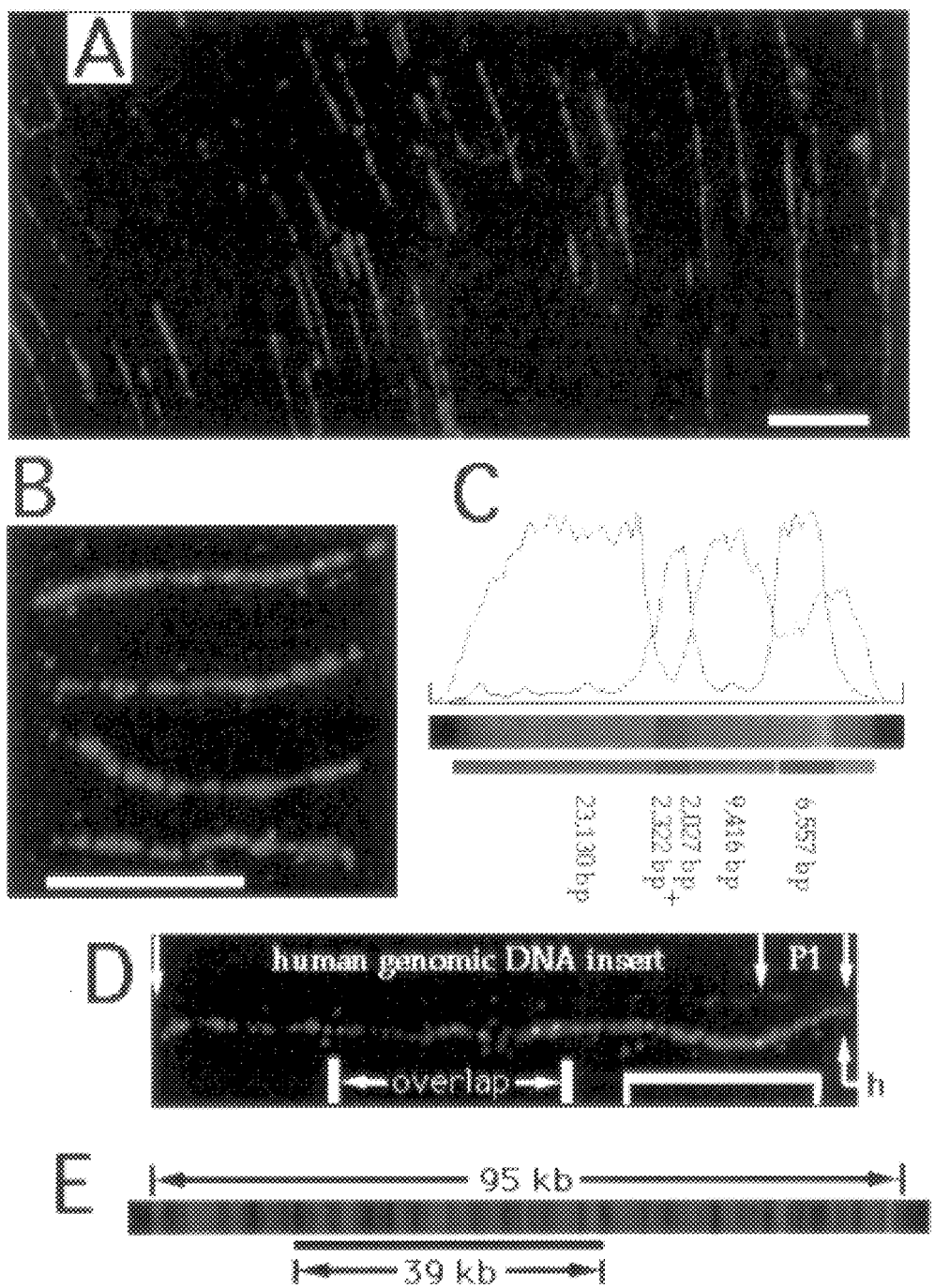
FIG. 2A shows a color image produced following hybridization and detection of fluorescently labeled HindIII restriction fragments to stretched lambda DNA fibers; a field showing numerous hybridized fibers is shown.
FIG. 2B shows an enlarged view of the stretched and hybridized lambda fibers shown in FIG. 2A.
FIG. 2C shows the longitudinal profiles of red and green fluorescence produced by averaging the signals from 45 individual lambda fibers hybrided with labeled HindIII restriction fragments (top) and a color code bar generated from the fluorescence profiles (middle); a panel depicting the predicted hybridization domains is shown under the color code bar (bottom).
FIG. 2D shows an image produced following FISH of RMC17P036 DNA fibers (P1 clone) with a labeled pBHp53-2 probe (cosmid) and a labeled RMC17P036 probe.
FIG. 2E depicts an alignment of 11 RMC17P036 P1 molecules hybridized with the pHBp53-2 cosmid probe in combination with the RMC17P036 P1 probe.

The preparation of labeled HindIII fragments was performed as described in Example 2 below. Hybridization, washing and detection of probe bound to the stretched DNA on the two glass surfaces was conducted as described in Example 2 below. FIG. 2C (described below) shows the hybridization pattern expected from the specific binding of the labeled restriction fragments to the stretched lambda fiber. FIGS. 1A and 1B show images obtained following FISH to lambda fibers stretched on either a vinyl-trichlorosilane-treated coverslip or a APS-treated slide, respectively. The images shown in FIG. 1, Panels A and B are shown at the same resolution.

Examination of the resulting images showed that the results obtained using the APS-derivatized slides (FIG. 1A) were superior to those obtained using the vinyl-trichlorosilane-treated coverslips. In particular, use of the vinyl-trichlorosilane-treated coverslips resulted in an unacceptably high background. From additional experimentation it is known that the detection reagents used (avidin-FITC and rhodamine-labeled anti-digoxigenin antibody) do not bind to the treated glass surfaces to a significant degree. Therefore, the background fluorescence seen in FIG. 1A (i.e., the small dots and stretches of red and green fluorescence scattered throughout the field which is not hybridized along a linear DNA fiber) is most likely due to the binding of the detection reagents to biotinylated or digoxigenin-containing DNA (i.e., the probes). It is not known whether the high background observed is due to the binding of the probe DNA directly to the treated glass surface or whether the background is cause by excessive fragmentation of the DNA fiber during the stretching, denaturation, hybridization and/or washing steps. Fragments of the DNA fiber which move from their original position in a DNA fiber which then bind the probe DNA followed by binding of the detection reagents could also produce the pattern of background hybridization seen when vinyl-trichlorosilane-treated coverslips are used during FISH to stretched DNA fibers.

Regardless of the exact mechanism, the use of vinyl-trichlorosilane-treated coverslips produces unacceptable levels of background fluorescence in FISH experiments. A high background reduces the contrast between areas of alternating green and red fluorescence (i.e., the boundary areas) and thus the definition of the boundary between the region of hybridization between two adjacent probes (or one probe and the underlying fiber) becomes difficult to assign. This leads to the definition of arbitrary boundaries during the interactive tracing of hybridized fibers (i.e., during mapping where the user defines the boundary as described below). Unacceptable background levels exist when the background is so high that the boundary or the ends of the fiber cannot be detected within 1–2 µm. Following FISH using DNA fibers combed on vinyl-trichlorosilane-treated coverslips, the majority of the fluorescence observed on the coverslip was due to the binding the labeled probes to the glass surface rather than to the DNA fibers.

In addition to the high background observed, fewer stretched and hybridized intact or full-length lambda DNA fibers were present per filed of view when the vinyl-trichlorosilane-treated coverslips were used in comparison to the results obtained using APS-treated slides (FIG. 1B).

FIG. 1B shows representative results obtained when lambda DNA fibers were combed on APS-treated slides followed by FISH. As seen in FIG. 1B, the majority of fluorescence observed following FISH of fibers stretched on APS-treated slides is due to the presence of labeled probe bound to the stretched lambda fibers (i.e., there is a low level of background fluorescence). The ends of the lambda fibers are clearly visible and the boundaries between areas of binding probes labeled with FITC (green) or rhodamine (red) are easily detectable.

The above experiments demonstrated that treatment of glass surfaces with 3-aminopropyltriethoxy silane (APS) produced superior results. It is noted that the same DNA preparation was placed on the vinyl- or APS-treated glass surfaces so that differences in the level of background observed is not attributable to differences in the integrity of the DNA preparations. In addition, similar results are obtained using APS-treated coverslips so that the fact that a vinyl-treated coverslip was compared to an APS-treated slide in this experiment would have no effect on the results obtained.

In the above experiments the stained DNA was present in water and a high percentage of the DNA fibers appeared to be fragmented. It is noted the degree of fragmentation observed when vinyl-treated coverslips were employed was extreme; see FIG. 1A (no intact fibers are seen and very high levels of background are present). However, even with the APS-treated slides, numerous lambda fibers appeared to be truncated (compare FIG. 1B with the intact fibers shown in FIG. 2B). In addition, photobleaching of YOYO-1 stained DNA occurred fairly rapidly. The fragmentation and rapid photobleaching of the stained DNA was prevented by placing YOYO-1 stained DNA into antifade (AF)-solution (1% p-phenylenediamine, 15 mM NaCl, 1 mM $H_2PO_4$, pH 8.0, 90% glycerol). The use of AF-solution reduced the breakage (fragmentation) of DNA molecules during the stretching procedure and reduced photobleaching during microscopic analysis.

The AF solution reduced DNA breakage and allowed the samples to be stored at room temperature for 24 hours without visible breakage. However, the AF solution was found to substantially reduce binding of the DNA molecules to the solid substrate (i.e., the APS-treated slide) and the high glycerol concentration prevented drying. Further dilution of this suspension with water at a ratio of 1:10, allowed DNA binding and permitted good stretching when the slide was dried at room temperature.

d) Optimized Molecular Combing Procedure i) Preparation of APS-Derivatized Slides Glass slides were cleaned in equal parts of concentrated hydrochloric acid and methanol for at least 30 minutes followed by overnight immersion in 18M sulfuric acid. The slides were then washed in 8–10 changes of ultrapure water, immersed in boiling water for 10 minutes and air dried. Cleaned slides were placed in a 10% solution of 3-aminopropyltriethoxy silane (APS; Sigma) in 95% ethanol for one hour, rinsed several times (8–10) with water, washed with 100% ethanol and air dried. Prior to use, slides were heated to 80°–110° C. overnight. Slides prepared in this manner are herein referred to as APS-derivatized slides.

ii) Preparation of DNA and Molecular Combing

DNA molecules which are to be subjected to molecular combing are isolated using standard techniques which are appropriate for the size of the DNA molecule to be examined. For example, DNA molecules less than 25 kb in size may be isolated by standard extraction procedures (e.g., alkaline lysis of host cells containing plasmid, phage or cosmid constructs). If the DNA of interest is not in a linear form, then the isolated circular DNA may be linearized by digestion with a restriction enzyme which cuts the DNA molecule once (preferably within vector as opposed to insert sequences). However, as shown in Example 4 below, molecular combing may be conducted using circular DNA molecules.

The extracted or extracted and linearized DNA may then be further purified by electrophoresis on agarose gels. Typically, the size of the DNA molecule to be combed will be in excess of about 17 kb and standard agarose gel electrophoresis cannot be employed for the isolation of large (greater than about 25 kb) linear DNA fragments due to poor resolution of large DNA fragments in this system.

To prepare DNA fragments 17 to 2000 kb in size for molecular combing, the following procedures may be employed. DNA is extracted from host cells containing P1 clones, YACs or BACs using standard alkaline lysis procedures (described in Example 3 below). When the DNA of interest is contained within a circular vector such as a P1 construct, the isolated DNA may be linearized using a restriction enzyme which cuts the clone at a single location (and preferably within the vector sequences). The linearized DNA is then purified by pulsed-filed gel electrophoresis (PFGE). PFGE may be conducted as either field inversion electrophoresis or contour-clamped homogeneous electric field (CHEF) electrophoresis. CHEF is advantageous when very large DNA molecules are to be resolved (greater than about 2000 kb).

For example, PFGE may be conducted using the CHEF Mapper II PFGE apparatus (BioRad) according to the manufacturer's instructions [1.0 to 1.5% LMP agarose (Gibco-BRL) may be used for isolation of YAC DNA by PFGE]. A band containing the linearized P1 clone is then excised and the agarose is removed by digestion of the gel slice with β-agarase I (agarase; NEB) using 2 units of agarase in 200 μl agarase buffer (NEB) according to the manufacturer's instructions. A 1 μl aliquot containing approximately 0.5–1.0 ng of the isolated P1 clone DNA is then mixed with 1 μl of 1 μM YOYO-1 in $H_2O$, 0.001% DMSO and 9 μl of AF-solution [the 1 μM solution of YOYO-1 is made fresh daily by dilution of the stock YOYO-1 solution (1 mM in DMSO as supplied by the manufacturer, Molecular Probes)]. This mixture is then diluted 1:10 with water and 1–4 μl of the diluted solution is placed upon an APS-derivatized slide and molecular combing is conducted as described below.

For large DNA molecules present in a linear form, such as that contained within YAC clones (comprising DNA molecules having a size of about 100 to 2000 kb), the DNA may be isolated by field inversion gel electrophoresis as described above. Following electrophoresis, gel slices containing the YAC are excised from 1% low melting point agarose gels and the agarose is removed using agarase digestion as described above. Following agarase digestion, the YAC DNA is dialyzed for 2 hours against 100 mM NaCl on a floating dialysis filter as described [Schedl, et al., *Nature* 362:258 (1993)] with the modification that a Millipore Minitan-S polysulfone membrane filter (100,000 NMWL) was used for microdialysis.

The dialyzed YAC DNA is then diluted with water to 1.2 ng/l and mixed with an equal volume of YOYO-1 (1 μM) and 8 volumes of AF-solution. After a 3 minute incubation at 20° C., the DNA is further diluted 1:10 with water. Two microliters of this DNA containing approximately 24 pg or 30,000 full length molecules is placed on a non-treated 22 mm×22 mm coverslip. An APS-derivatized slide is then placed on top and the liquid was allowed to dry at 4° C. overnight.

When DNA fibers are to be microdissected following hybridization (FISH), the DNA fibers are stretched using APS-treated coverslips (borosilicate) rather than APS-treated slides. The solution containing the DNA to be stretched is placed on the treated coverslip and an untreated coverslip. The solution is allowed to dry thereby causing stretching of the DNA fibers.

Target DNA need not always be placed into AF-solution (at a 1:10 dilution) prior to molecular combing (stretching). The use of AF-solution is desirable when the integrity of the DNA preparation (stained with YOYO-1) is to be assessed by fluorescence prior to stretching (e.g., for assessment of the integrity of YAC DNA following PFGE or assessment of the degree of linearization of P1 clones following restriction digestion). When the DNA preparation need not be examined prior to stretching, the DNA to be combed is placed in water rather than diluted AF-solution (and staining with YOYO-1 is omitted). The use of water in place of diluted AF-solution permits the complete and somewhat more rapid drying of the stretched DNA fibers prior to FISH. When DNA preparations are stretched in the absence of AF-solution, drying is conducted at 4° C.; when the DNA is present in AF-solution (1:10), drying is conducted at room temperature (approximately 20° C.) or at 4° C.

EXAMPLE 2

High Resolution Mapping of Lambda Restriction Fragments along the Lambda Phage DNA Molecule The above example demonstrated conditions which allow optimal molecular combing of large DNA fragments. The ability to use these combed DNA fragments for the accurate mapping of specific DNA sequences along a stretched (i.e., combed) DNA molecules was first examined using the approximately 49 kb long lambda phage DNA molecule.

The accuracy and precision with which DNA could be mapped and sized using quantitative DNA fiber mapping was assessed by hybridizing 4.3 kb, 6.6 kb, 9.4 kb and 23 kb lambda DNA/HindIII fragments to combed lambda phage DNA. The 4.3 kb fragment represents a mixture of the 2.0 and 2.3 kb HindIII restriction fragments. A commercially available preparation of high molecular weight lambda DNA of unknown integrity was used in these studies (Sigma). Restriction fragments of lambda DNA were prepared by digestion of high molecular weight lambda DNA with HindIII (Gibco-BRL); the digestion was conducted using 10 units of HindIII/μg of lambda DNA according to the manufacturer's instructions. The restriction fragments were separated by electrophoresis on a 2% low melting point agarose gel and the individual fragments were excised from the gel (with the exception of the 2.3 and 2.0 kb fragments which were excised as a single band). Agarose was removed by digestion with agarase as described in Example 1.

Approximately $1\times10^7$ lambda DNA molecules (Sigma) were stained with 0.5 µM YOYO-1 as described in Example 1. Briefly, one microliter of a solution containing $1\times10^7$ lambda molecules/µl in water was mixed with 1 µl of YOYO-1 (1 µM in H$_2$O, 0.001% DMSO) and 8 µl AF-solution. This suspension was then further diluted with water at a ratio of 1:10. The equivalent of approximately $1\times10^6$ full length lambda DNA molecules (contained within 1 µl) was deposited on an APS-derivatized slide (prepared as described in Ex. 1). A round 18 mm coverslip was placed over the DNA solution and the solution was allowed to dry overnight at 20° C.

The isolated HindIII restriction fragments were labelled as follows. The 9.4 kb and 23 kb probes were labeled with biotin (biotin-14-dCTP; Gibco-BRL) and the 4.3 kb (i.e., the mixture of the 2.3 and 2.0 kb fragments) and 6.6 kb probes were labeled with digoxigenin (digoxigenin-dUTP; BM) using a random primer extension kit according to the manufacturer's instructions (BioPrime DNA Labeling System; Gibco-BRL).

The labeled HindIII fragments were then hybridized overnight to the combed lambda DNA fibers as follows. Approximately 20 ng of each probe in 10 µl of 55% formamide (Gibco-BRL), 10% dextran sulfate, 100 ng/µl salmon sperm DNA in 2x SSC (300 mM NaCl, 30 mM Na citrate, pH 7.0) was applied to a slide containing combed lambda DNA fibers. A coverslip was placed over the solution. Denaturation was performed by incubating the coverslipped slide at 100° C. for 3 minutes; this was achieved by placing the slide onto a hot plate. Following the denaturation step, the probes were allowed to hybridize overnight at 37° C. in a humidified chamber. The slides were then washed in three changes of 2x SSC at 20° C. for 15 minutes per wash with slight agitation. The presence of the bound biotinylated or digoxigenin-containing probes were detected by conjugation with avidin-FITC (Vector) and a rhodamine-labeled sheep antibody directed against anti-digoxigenin (BM), respectively. Briefly, the biotinylated probe was detected with a 20 minute incubation at room temperature in avidin-FITC (5 µg/ml in PNM [0.1M sodium phosphate, pH 8.0, 0.1% nonidet-P40, 5% nonfat dry milk (Carnation) and 0.02% sodium azide]). The digoxigenin-containing probe was detected by the addition of the rhodamine-labeled sheep antibody directed against anti-digoxigenin (20 µg/ml in PNM) to the mixture containing the avidin-FITC. Excess avidin-FITC or rhodamine-labeled sheep antibody directed against anti-digoxigenin was removed by washes in two changes of 2x SSC at 20° C. (room temperature).

The hybridization signals were then amplified using biotinylated goat-anti-avidin (Vector) followed by a second layer of avidin-FITC (5 µg/ml in PNM) and a Texas-Red-labelled rabbit antibody directed against sheep IgG (Vector) (20 µg/ml in PMN) as described above for staining with the avidin-FITC/rhodamine-labeled sheep antibody directed against anti-digoxigenin mixture.

The slides were then washed twice in 2x SSC and mounted in AF-solution for microscopic inspection. Image analysis was performed by acquiring images on a quantitative image processing system based on a Zeiss fluorescence microscope equipped with 63x, 1.25 NA and 40x, 1.3 NA oil objectives, a Photometrics cooled CCD camera, multiband-pass filters for simultaneous observation of FITC and Texas red or AMCA/DAPI (Chroma Technology) and a SPARC workstation (SUN) [Kallioniemi, et al., *Science* 258:818 (1992)]. AMCA (7-amino-4-methylcoumarin-3-acetic acid) (Molecular Probes) is a fluorescent dye that excites in the ultraviolet (350 nm) and emits in the visible (450 nm) producing an intense blue fluorescence.

Images of stretched lambda molecules of about 21.6 µm were acquired at 63x magnification. Forty-five molecules of approximately full-length which did not overlap with other DNA fibers were selected for analysis. The longitudinal fiber axis was traced interactively and a computer program calculated integrated fluorescence for 9 pixel wide cross-sections equivalent to 1.0 µm along the selected path. Fluorescence profiles were aligned manually based upon the minimum of red fluorescence in the 9.4 kb segment (FIG. 2C, described below). Profiles were averaged and the position of the 10, 50 and 90% values were calculated for the peaks in the longitudinal fluorescence profiles. Map positions were determined by first calculating the ends of the linear molecules. The points where the fluorescence of the flanking green fragments had decreased to 10% of its peak value was defined as the molecule endpoints; this gave a measure of 200 pixels for the lambda molecule length and a conversion factor of 2.26 kb/µm. Pixel spacing was 0.1079 µm/pixel. The positions where the fluorescence of the 4.3, 9.4 and 6.6 kb fragments had reached 50% of their maximal value was used to define the boundaries of these labelled fragments. The difference between the measured boundaries and the exact position of the HindIII restriction sites was defined as the accuracy of the measurement. The interval between the 10 and 90% values was calculated from the physical distance between fragment boundaries (the 50% values) multiplied by 2.26 kb/µm.

Hybridization of the HindIII restriction fragment probes to combed phage DNA molecules is shown in FIGS. 2A–2C. In FIG. 2A, a field showing numerous combed and hybridized lambda fibers is shown; the white bar provides a size marker and represents 10 µm. Probes generated using biotin (i.e., the 9.4 and 23 kb fragments) appear green and probes generated using digoxigenin [i.e., the 4.3 (i.e., the mixture of the 2.3 and 2.0 kb fragments) and 6.6 kb fragments] appear red.

FIG. 2B provides an enlarged view of the combed and hybridized lambda fibers shown in FIG. 2A; the white bar represents 10 µm. FIG. 2B demonstrates the reproducibilty of this technique. As shown in FIGS. 2A and 2B, the hybridization efficiency was uniformly high and most molecules showed alternating red and green fluorescing domains in the regions homologous to the probes as expected (FIG. 2B). The molecules shown in FIG. 2B are approximately full-length. The green fluorescence seen distal to the 6557 bp (6.6 kb) fragment is due to impurities (partial digests) contained in the preparation of the 23 kb fragment probe.

FIG. 2C shows the longitudinal profiles of red and green fluorescence produced by averaging 45 lambda DNA molecules (top of figure). Individual profiles were not normalized. Fluorescence profiles (top) were used to generate a color code bar (center of figure). The bottom portion of FIG. 2C shows the predicted hybridization domains based on the known locations of the HindIII fragments in the phage DNA sequence.

Examination of the hybridized lambda fibers showed that using this commercial preparation of lambda DNA only three to four percent of the molecules were intact and showed the predicted hybridization pattern. The other molecules were shorter and showed hybridization pattern as expected from truncated lambda DNA molecules. This was not a limitation because of the high density of fibers. On average, several full length lambda molecules were observed per field of view using a 63× microscope objective. The intact fibers were ~21.6 μm in length indicating that the 48.9 kb molecules were stretched to 2.26 kb/μm.

The reproducibility with which the probes could be mapped and sized was quantitatively analyzed. Forty-five different lambda fibers of approximately full length were analyzed using digital imaging microscopy. The mean distances of the boundaries of the 4.3 kb, 6.6 kb and 9.4 kb HindIII fragments from the phage molecule endpoints were within 2 kb of the known distances and the mapping precision was better than 3 kb for all measurements. The reproducibility of the quantitative fiber mapping technique of the present invention is illustrated in FIG. 1C, which shows red and green profiles produced by averaging red and green fluorescence profiles measured from 45 individual DNA fibers. The sizes of the internal 4.3 kb, 6.6 kb, and 9.4 kb fragments were estimated from measurements of the length of their hybridization domains along the 45 individual lambda molecules to be 4.1+/−1.3 kb 5.9 kb+/−1.5 kb and 9.7 kb+/−1.5 kb, respectively (assuming that the DNA molecules were stretched to 2.26 kb/μm).

The above results demonstrated that the quantitative DNA fiber mapping technique allowed the mapping of restriction fragments along the approximately 49 kb long lambda phage DNA molecule with approximately 2 kb precision. It is noted that internal standards need not be used when mapping probes using the quantitative DNA fiber mapping technique. As shown above, this technique results in the uniform stretching of the DNA fibers along the length of the stretched molecule thereby obviating the need for internal standards to control for non-uniform stretching of DNA fibers.

EXAMPLE 3

Quantitative DNA Fiber Mapping Allows the Accurate Localization of Clones to Large Combed DNA Molecules The increasing availability of mapped large insert clones (e.g. YACs, BACs and P1s) allows ready assembly of smaller insert sequence-ready contigs from the larger insert clones. A contig comprises groups of clones which represent overlapping regions of a segment of the genome. In order to reduce the need to sequence redundant stretches of the genome, clones within a contig must be ordered to find a set of clones which contain the minimum overlap with other clones and yet span the entire region of interest (i.e., a minimally spanning contig or a contig which represents the minimal tiling path). In a typical study, the large insert clone either may be subcloned or used to select smaller insert clones from a genomic library. Either way, assembly of the resulting subclones into a minimally spanning contig is required for further analysis. Complete closure of the map requires identification and characterization of any gaps. The utility of FISH of the smaller clones to the larger combed DNA molecules is demonstrated herein using two examples: a) the localization of the overlap between a cosmid clone and a co-linear P1 clone and b) the mapping of P1 clones along an approximately 490 kb YAC with approximately 5 kb precision and estimation of the approximately 25 kb gap between these clones.

a) Localization of the Overlap Between a Cosmid Clone and a Co-linear P1 Clone

The DuPont human P1 library was screened to isolate a P1 clone containing a large insert containing sequences associated with the human p53 gene [Access to and screening of the DuPont is available through commercial vendors (e.g., Genome Systems, Inc. St. Louis, Mo.)]. PCR screening of the DuPont P1 library was conducted as described by Weier, et al. [Genomics 26:390 (1995)] with the exception that primers corresponding to sequences located within exons 5 and 8 of the human p53 gene were used for the screening of the P1 library. These primer pairs comprised: for the exon 5 target, p5351: 5'-TTCCTCTTCCTGCAGTACTC-3' (SEQ ID NO:1) and p5352: 5'-GCCCCAGCTGCTCACCTACG-3' (SEQ ID NO:2) and for the exon 8 target, p5381: 5'-CCTATCCTGAGTAGTGGTAA-3' (SEQ ID NO:3) and p5382: 5'-GCTTACCTCGCTTAGTGCTC-3' (SEQ ID NO:4). The use primers having sequences identical to these four primers have been used previously in studies of mutations in the p53 gene [Reiter, et al., Cancer Res. 53:3092 (1993) and Sato, et al., Cancer Res. 53:2944 (1993)].

PCR screening of the P1 library (DuPont) was performed using pair of Perkin-Elmer 9600 thermal cyclers. The PCRs contained 10 mM Tris-HCl, pH 8.3, 50 mM KCl, 1.5 mM $MgCl_2$, 100 nM each primer and 25 units/ml AmpliTaq (Perkin-Elmer). Thirty-five cycles comprising 94° C. for 30 sec; 57° C. for 30 sec; and 72° C. for 30 sec were conducted. The reaction products were fractionated on a 3% agarose gel and plate and position positives identified [The DuPont library comprises a series of microtiter plates containing pools of clones in each well. Once a pool containing a positive clone is identified, that pool is screened to identify a single positive clone. The screening of P1 libraries in this manner is standard in the art. See, for example, Shepard et al., supra and Weier et al., Genomics 26:390 (1995)].

P1 clones which produced products of the expected size (about 214 bp for the exon 5 primer pair and about 157 bp for the exon 8 primer pair) for both the exon 5 and exon 8 primer pairs were selected. Using this PCR screening procedure, clone RMC17P036 was isolated. Clone RMC17P036 has a total size of approximately 95 kb and contains an insert of approximately 78 kb including exon 5 and exon 8 of the human p53 gene.

A cosmid clone, termed pBHp53-2, containing a portion of the p53 gene sequences found on the P1 clone RMC17P036 was obtained from Dr. R. White (University of Utah). The pBHp53-2 probe is a part of a three cosmid contig for the human p53 gene.

i) Preparation of P1 Clone RMC17P036 DNA Fibers

DNA from clone RMC17P036 was isolated by alkaline lysis [Birnboim and Doly, Nucl. Acids Res. 7:1513 (1979)]. Briefly, an overnight culture of RMC17P036 was grown in 30–35 ml of TB medium (12 g/l bacto-tryptone; 24 g/l bacto-yeast extract; 4 ml/l glycerol; 100 ml/l 0.17M $KH_2PO_4$, 0.72M $K_2HPO_4$) containing 50 μg/ml kanamycin. An aliquot (18–20 ml) of the overnight culture was centrifuged in an Oakridge tube at 3400 rpm in a SS34 rotor (Sorvall) for 10 min. at 4° C. and the supernatant was discarded. The pellet was suspended in 2.34 ml of Solution I (50 mM glucose, 10 mM EDTA; 25 mM Tris-HCl, pH 8.0) and 100 μl of lysozyme stock (50 mg/ml in 10 mM Tris-HCl, pH 7.5). This mixture was incubated for 5 minutes at room temperature, then the tubes were placed on ice. Then 5.2 ml of Solution II (0.2N NaOH, 1% SDS) was added and the solutions were mixed by gentle inversion and incubated on ice for 5 minutes. Next, 3.8 ml of Solution III (3M NaOAc, pH 4.8) was added and the contents were mixed gently by inverting the tube a few times. This mixture was incubated on ice for 10 minutes. The tubes were then centrifuged for 15 minutes at 14,000×g. The supernatant (10.4 ml) was transferred to a fresh tube and 5.8 ml of isopropanol was added and the contents were mixed gently by inverting the tubes a few times. The mixture was centrifuged for 5 minutes at 14,000×g and the DNA pellet was washed with 70% ethanol. The pellet was then briefly air dried for 20–40 minutes at room temperature. The dried pellet was then suspended in 0.8 ml of TE buffer (10 mM Tris-HCl, 1 mM EDTA, pH 8.0). The DNA solution was then extracted with once with an equal volume of phenol/chloroform/isoamyl alcohol (25:24:1) followed by one extraction with chloroform/isoamyl alcohol. The extracted DNA solution was then precipitated with 100% ethanol and the pellet was washed with 70% ethanol. The washed pellet was resuspended in TE buffer (pH 7.4) containing 10 $\mu$g/ml RNase (BM). The mixture was incubated for 30 minutes at 37° C. The DNA was stored at −20° C.

An aliquot of the isolated P1 clone DNA (1 $\mu$g) was linearized with 10 units of NotI (BM) for 30 min. at 37° C. according to the manufacturer's instructions and purified by pulse field gel electrophoresis. Bands were excised and gel slices were treated with 2 units agarase in 200 $\mu$l agarase buffer (according to NEB's instructions). An aliquot of 1 $\mu$l containing approximately 0.5–1 ng of P1 clone DNA was mixed with 1 $\mu$l of $10^{-6}$M YOYO-1 and 9 $\mu$l of AF-solution and diluted 1:10 with water. Molecular combing was performed using APS-derivatized slides as described in Example 2; drying was conducted at 20° C. overnight.

ii) Preparation of Labeled pBHp53-2 DNA

Cosmid DNA was isolated from overnight cultures of clone pBHp53-2 using alkaline lysis as described above. Aliquots (400 ng) of pBHp53-2 DNA were labelled by random priming in the presence of digoxigenin-dUTP as described in Example 2.

iii) Preparation of Biotin-Labeled RMC17P036 DNA

In order to counterstain the combed RMC17P036 DNA fiber, biotin-labelled RMC17P036 DNA was prepared. P1 clone DNA was isolated from overnight cultures of clone pBHp53-2 using alkaline lysis as described above. Aliquots (400 ng) of RMC17P036 DNA were labelled by random priming in the presence of biotin-14-dCTP as described in Example 2.

iv) Hybridization of Digoxigenin-Labelled pBHp53-2 DNA and Biotin-Labeled RMC17P036 DNA to Combed RMC17P036 DNA Fibers Approximately 20 ng of each the labeled pBHp53-2 and RMC17P036 probes in 10 $\mu$l of 55% formamide (Gibco-BRL), 10% dextran sulfate, 100 ng/$\mu$l salmon sperm DNA in 2× SSC (300 mM NaCl, 30 mM Na citrate, pH 7.0) was applied to a slide containing combed RMC17P036 DNA fibers. A coverslip (untreated 18 mm, round) was placed over the solution. Denaturation, hybridization and washing was carried out as described in Example 2. Hybridization signals were amplified as described in Example 2 (i.e., detected with avidin-FITC and rhodamine-labeled sheep antibodies against digoxigenin followed by amplification of the initial signal using biotinylated goat-anti-avidin followed by a second layer of avidin-FITC and a rhodamine-labeled antibody against sheep IgG). Slides were then washed twice in 2× SSC and mounted in AF-solution for microscopic inspection.

Image analysis was performed as described in Example 2. Images from the hybridized P1 molecules were recorded using the 63× lens. A representative hybridization result is shown in FIG. 2D. The protocol deposited the high molecular weight P1 molecules at an average density of about one full-length P1 molecule every one to two fields of view, so that image acquisition could be done rapidly.

In FIG. 2D, hybridization of the cosmid DNA to the stretched P1 molecules delineates homologous regions. The size bar (white bar) indicates 10 $\mu$m. A probe generated from the pBHp53-2 cosmid clone is visualized in red. The P1 specific probe (green) was hybridized to counterstain the P1 molecule. This image of a single hybridized P1 molecule is part of a larger field containing several P1 molecules. The region of overlap (red fluorescence) is indicated ("|←overlap→|"). The location of the human genomic DNA insert within the P1 clone is indicated by labelling above the stretched fiber. The location of P1 vector sequences is also indicated by labelling above the fiber. A 493 bp region of high homology ("h") is located close to the unique NotI site located in the pAD10SacBII P1 vector (DuPont).

An alignment of 11 individual P1 molecules hybridized with the cosmid probe (red) in combination with the P1 DNA (green) is shown in FIG. 2E. The homologous region was found to be approximately 39±4 kb, based upon the total length of the P1 molecule (95 kb).

Alignment of the 11 images was facilitated by the presence of a region with high homology between cosmid and P1 DNA at one end of the fiber immediately flanking the NotI site (labeled "h" in FIG. 2D). A database search identified this region as a 493 bp stretch with 100% homology between the pAD10SacBII P1 vector and the pWE15 cosmid vector.

In addition to the region of high homology ("h" in FIG. 2D), several sites of weaker cross-hybridization between the cosmid and the P1 DNAs caused by Alu-type repeats in the cosmid and P1 insert were found. The sites of cross-hybridization caused by Alu-DNA repeats showed up as small yellow spots along the fibers (FIG. 2D). The presence of Alu-type repeat elements in probe pBHp53-2 was further verified by hybridization of digoxigenin-labeled pBHp53-2 DNA to normal human metaphase spreads which generated a strong Alu-specific pattern [Kornberg and Rykowski, Cell 53:391 (1988)]. Furthermore, hybridization of a cloned Alu DNA probe (PV92) [Matera, et al., *Nucleic Acids Res.* 18:6019 (1990)] to fibers of clone RMC17P036 confirmed the localization of Alu repeat clusters on the P1 molecules (see Example 7 for experiments demonstrating the mapping of the Alu repeat clusters within the P1 clone).

Figure 3:
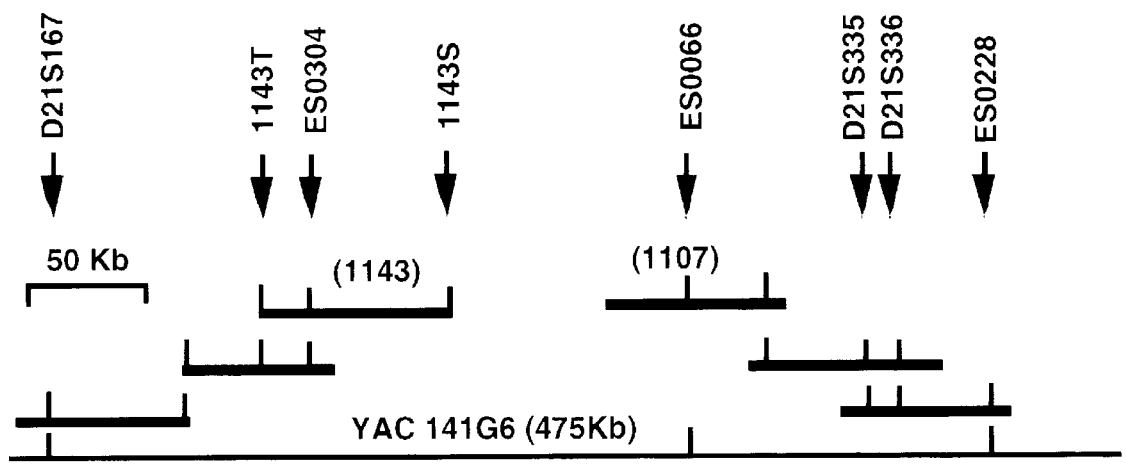
FIG. 3 shows a map based on STS content mapping of P1 clones '1107' and '1143' and the YAC clone '141G6'; this map shows the relative position of the P1 clones and the gap region between two flanking P1 contigs. The scale bar represents 50 kb.

The results shown above demonstrate that FISH of a smaller co-linear cosmid clone to a larger combed P1 clone allowed the localization of the region of homology between these clones to be accurately and precisely determined.

b) High Precision Mapping of P1 Clones Along an Approximately 490 kb YAC and Estimation of the Gap Between These Clones The utility of quantitative DNA fiber mapping for longer range mapping was examined by determining the precision with which two P1 molecules designated '1107' and '1143' could be mapped along a ~490 kb YAC clone termed '141G6' [Chumakov, et al., *Nature* 359:380 (1992)]. These P1 molecules were known from STS content mapping to overlap with the YAC but not with each other. FIG. 3 shows a map based on STS content mapping of P1 clones '1107' and '1143' and the YAC clone '141G6'; this map shows the relative position of the P1 clones and the gap region between two flanking P1 contigs.

The P1 clones '1107' and '1143' were isolated from a human genomic P1 library [Shepard, et al., *Proc. Natl. Acad. Sci. USA* 91:2629 (1994)] in the course of assembly of a P1-based map by STS content mapping. The sizes of the human genomic insert in P1 clones were calculated from the pulse field gel electrophoretic analysis of NotI linearized recombinant P1 molecules. The size of the P1 cloning vector pAD10SacBII is ~17 kb.

High molecular weight YAC DNA from clone '141G6' to be used for molecular combing was isolated by suspension and lysis of yeast cells in agarose plugs followed by PFGE. Briefly, freshly picked YAC colonies (about 15) were picked and placed into 15 ml of AHC media. The culture was grown at 30° C. overnight. The cells were then collected by centrifugation at 4000 rpm in a SS34 rotor (Sorvall) for 6 minutes at 4° C. The pellet was resuspended in 0.5 ml of 0.125M EDTA, pH 7.8 and transferred to a microcentrifuge tube. The tube was centrifuged for 3 seconds in a microcentrifuge, the supernatant was removed and the pellet was allowed to stand for 5 minutes to level off. The volume of the pellet was estimated. [For haploid yeast strains, 70 μl pellets are used; for diploid strains, 40 μl pellets are used.] Plug molds were assembled by adding 500 μl of SCE (1M sorbitol, 0.1M Na citrate, 10 mM EDTA, pH 7.8) to a 70 μl cell pellet and the pellet was resuspended. Five hundred microliters of 1.5% LMP agarose (Gibco-BRL) at 49° C. was added and the mixture was pipetted up and down, then vortexed for 1–2 seconds to suspend the yeast cells. Aliquots (100 μl) were dispensed into molds (BioRad) and the molds were refrigerated (4° C.) for 10 minutes. The plugs were then placed into 2 ml of SCE containing 100 μl of Zymolase (ICN; 70,000 units/g, 10 mg/ml in 50 mM KPO$_4$, pH 7.8, 50% glycerol stored at −20° C.) and shaken at 150 rpm at 30° C. for 2.5 hours to overnight. The SCE/Zymolase solution was removed and 2 ml of ES (0.5M EDTA, pH 8.0, 1% sarcosyl) and 100 μl of proteinase K (20 mg/ml in 10 mM Tris-HCl, pH 7.5) was added. The tubes were shaken for 5 hours to overnight at 50° C. The ES/proteinase K solution was removed and the plugs were rinsed 5 times with 6 ml TE50 (10 mM Tris-HCl, pH 7.5; 50 mM EDTA, pH 7.8) for 30 minutes per rinse or until no more sarcosyl was present. The plugs were stored at 4° C. in TE50.

Plugs containing the YAC DNA were subjected to pulsed field gel electrophoresis (PFGE) using a BioRad CHEF Mapper II PFGE apparatus according to the manufacturer's instructions for the isolation of high molecular weight DNA. Southern blot analysis of clone '141G6' indicated a YAC size of approximately 475 kb. Slices containing the YAC were excised from the low melting point agarose (Gibco-BRL) and equilibrated in agarase buffer. The agarose was then removed by digestion with agarase as described in Example 2. The YAC DNA was then microdialyzed against 100 mM NaCl using a Millipore filter as described in Example 1. Following microdialysis, the YAC DNA was diluted with water to 1.2 ng/μl and mixed with an equal volume of YOYO-1 ($1 \times 10^{-6}$M) and 8 volumes of AF-solution. After a three minute incubation at 20° C., the DNA was diluted a further 1:10 with water. Two microliters of this DNA containing approximately 24 pg or 30,000 full-length molecules was placed on a untreated 22×22 mm coverslip. An APS-derivatized slide was then placed on top and the liquid was allowed to dry overnight at 4° C.

Labeled P1 probes were generated from DNA prepared from overnight cultures of clones '1143' and '1107' by alkaline lysis as described in Example 2. Aliquots (400 ng) of DNA isolated from these P1 clones were labelled by random priming in the presence of digoxigenin-dUTP as described in Example 2.

A biotinylated DNA probe for counterstaining the YAC molecule was generated by random priming of DNA isolated from the YAC containing yeast clone '141G6'. YAC DNA to be used as a probe was prepared as follows. Yeast cells containing the desired YAC clone (i.e., '141G6') were grown at 30° C. in 50 ml of synthetic complete (SC) dropout media (Ura-/Tryp-) in a 250 ml flask to saturation (about 24–60 hours). The cells were transferred to 50 ml tubes (Falcon) and pelleted by centrifugation at 2000 rpm in a swing bucket rotor (IEC) at 4° C. for 5 minutes. The cell pellet was resuspended in 3 ml of 0.9M sorbitol, 0.1M EDTA, pH 7.5 containing 4 μl of β-mercaptoethanol per 3 ml. One hundred microliters of 10 units/μl lyticase (in 1M sorbitol) was added and the mixture was incubated at 37° C. for 1 hour. The mixture was centrifuged as above and the supernatant was discarded. The pellet was resuspended in 5 ml of 50 mM Tris-HCl., pH 7.4, 20 mM EDTA; 0.5 ml of 10% SDS was added and the tube was inverted a few times to mix. The mixture was incubated at 65° C. for 30 minutes. Next, 1.5 ml of 5M potassium acetate was added and the mixture was placed on ice for 1 hour. The mixture was then distributed between 5 microcentrifuge tubes (Eppendorf) and the tubes were centrifuged for 10,000 rpm for 10 minutes at 4° C. in a microcentrifuge. The supernatant was transferred to an Oakridge tube and 2 volumes of 100% ethanol (at room temperature) was added and the tube was gently inverted a few times. The tubes were then centrifuged for 15 minutes at room temperature in a SS-34 rotor (Sorvall) at 5,000–6,000 rpm. The pellet was dried overnight at room temperature. The dried pellet was resuspended in 3 ml of TE buffer (pH 7.4) over about a 2 hour period with shaking. The mixture was then transferred to 1.5 ml microcentrifuge tubes (750 μl/tube) and an equal volume of phenol/chloroform/isoamyl alcohol was added and the tubes were vortexed. The phases were separated by centrifugation at low speed [e.g., MicroMax centrifuge (Hoefer, S. San Francisco) at 2000 rpm] for 5 minutes. The bottom layer was aspirated without disrupting the interphase. An equal volume of chloroform (750 μl) was added and the tubes were vortexed and centrifuged as above; the bottom layer was again aspirated and the tube was spun again. The supernatant was then transferred to 4 microcentrifuge tubes (1.5 ml) and 40 μl of a DNase-free RNase (BM) solution (1 mg/ml) was added and the tubes were incubated at 37° C. for 30 minutes. One volume of isopropanol was then added to each tube and the tubes were gently inverted to mix. The DNA was collected by centrifugation in a microcentrifuge for 10 minutes at 4° C. The pellet was washed with 1 volume of 100% ethanol and the pellet was dried overnight. The pellet was then resuspended in 20–50 μl of TE buffer (pH 7.4) and stored at −20° C.

Digoxigenin-labeled DNA from pYAC3 [a plasmid containing both YAC vector arms available from ATCC (ATCC #37520)] was included in the hybridization probe mixtures specifically to label the ends of untruncated YAC molecules.

The dual color detection scheme employed herein reveals regions of overlap as red/yellow stained regions, while parts of the YAC such as flanking sequences that do not bind the pYAC plasmid or the P1 probes appear in green. It should be noted that Cot-1 DNA, normally employed to block hybridization of repeated DNA sequences during FISH with large-insert human probes [Weier, et al., *Genomics* 26:390 (1995)] is not needed in this protocol because the repeats are widely distributed along the combed DNA fibers.

FISH was conducted using digoxigenin-labeled DNA from one or both P1 clones and combed YAC molecules along with a probe for the YAC vector arms (pYAC3) that flanked each end of the YAC and detected using rhodamine-labeled anti-digoxigenin. The YAC fiber itself was counterstained by hybridization with biotinylated total YAC DNA (i.e., '141G6') and detected using avidin-FITC. This scheme allowed identification of full length YAC molecules since these carried red fluorescence signals at each end (produced by hybridization of the pYAC3 sequences) as well as localization of the P1 probes along the individual fibers. The hybridization was carried out using approximately 20 ng of each probe as described in Example 2. Bound probes were detected by conjugation with avidin-FITC and a rhodamine-labeled sheep antibody against digoxigenin followed by amplification of the hybridization signals as described in Example 2. Slides were mounted in AF-solution for microscopic analysis.

Figure 4:
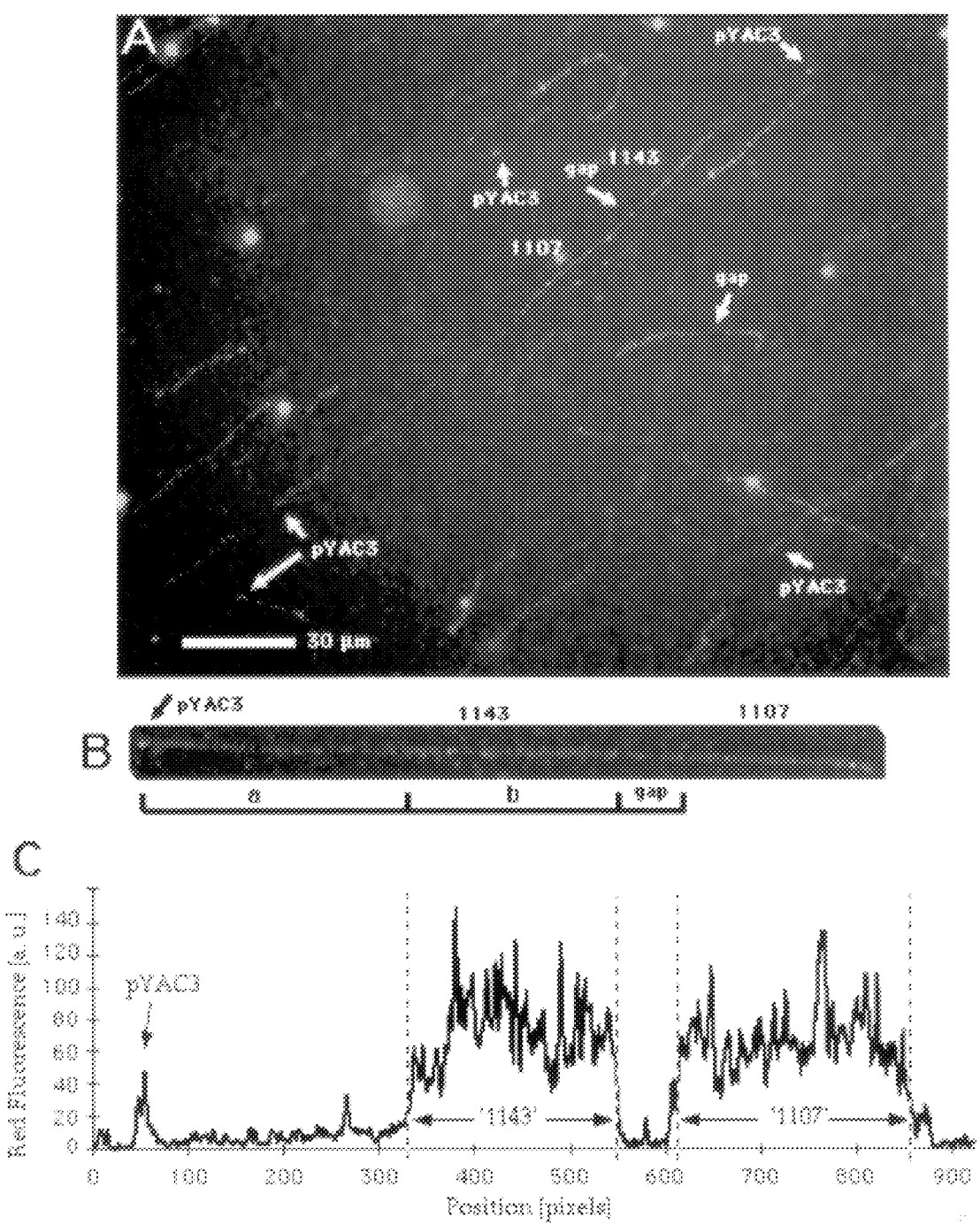
FIG. 4A an image (at three-fold reduction) produced following FISH of stretched YAC fibers ('141G6') with probes corresponding to pYAC3 (red), the '1143' P1 clone (red), the '1107' P1 clone (red) and the '141G6' YAC clone (green).
FIG. 4B depicts a typical YAC fiber hybridized as described in FIG. 4A at full resolution.
FIG. 4C shows the average of 10 red fluorescence profiles along individual YAC fibers hybridized as described in FIG. 4A.

Image analysis was conducted as described in Example 2. Images from the hybridized YAC molecules were recorded using the 40× lens. The pixel spacing for the 40× lens is 0.17 μm/pixel. Representative hybridization results are shown in FIGS. 4A–C. In FIG. 4A the spacebar is shown by the white bar labeled 30 μm. In FIG. 4A combed (straightened) molecules from the YAC clone '141G6' (shown by the green fluorescence) were hybridized with digoxigenin-labeled probes from P1 clones '1143' and '1107' (red fluorescence) and the plasmid pYAC3 containing the vector arms (red fluorescence). The hybridized P1 clones and the pYAC3 binding sites as well as the gap between '1143' and '1107' are indicated. The resolution of the recorded image was reduced threefold to produce a figure of the size shown here.

In FIG. 4B, a typical YAC DNA molecule (fragment) is shown at full resolution. The hybridization signals of plasmid pYAC3 and the two P1 probes '1143' and '1107' produce the red fluorescence and are indicated. The bar below the DNA fiber represents the distances ("a" and "b") along the YAC DNA fiber which were used for physical mapping of '1143' on YAC '141G6'. The interval labeled "gap" represents the size of the gap region between the P1 clones.

In FIG. 4C, the average of 10 red fluorescence profiles along individual YAC molecules is shown. Analysis of this average profile allowed the determination of the gap size between P1 clones '1143' and '1107'. The hybridized P1 clones, the proximal pYAC3 binding site and the approximate locations of 50% values of the red fluorescence (dotted vertical lines) are indicated.

The degree and uniformity of stretching achieved for the YAC molecules was assessed by measuring the lengths of the domains produced by hybridization with DNA from the ~81 kb P1 clone '1143' along 10 YAC fibers. The length of '1143' along the YAC fibers was 34.5 μm+/−2.55 μm, corresponding to stretching of 2.3 kb/μm, almost identical to that achieved for lambda phage (Example 2). This demonstrates that the degree of stretching is highly reproducible and independent of the length of the combed molecule.

One important use of quantitative DNA fiber mapping is precise localization of probe DNA molecules along the target DNA molecule. A representative image of a hybridized full length (~490 kb) YAC in FIG. 4A shows the locations of the two P1 probes, the extent of the gap between them and the terminal pYAC3 signals. Separate hybridizations of the two P1 probes showed that clone '1143' maps close to one end of '141G6', while clone '1107' maps close to the center of the YAC molecule (FIGS. 4A, 4B). These results agree well with the map generated by the independent method of STS content mapping (see FIG. 3).

The location of the P1 clone '1143' along the YAC was determined by measuring the distance of its hybridization signal from the end of the YAC marked by the pYAC3 signal (distance "a" in FIG. 4B). The hybridization domain of clone '1143' began at 49.2 μm or 114 kb (+/−5.7 kb) from the proximal end of the YAC and extended 81 kb, assuming a conversion factor of 2.3 kb/μm. Measurement of the hybridization domain of clone '1107' suggested a mean size of 89.9 kb (+/−8.2 kb), which agrees well with the size of 88 kb obtained by pulsed field gel electrophoretic (PFGE) analysis. This conversion also allowed the estimation of the size of the YAC as 496 kb (standard deviation: 37 kb, N=4). This is in good agreement with published values for this YAC clone which range from 430 kb to 495 kb [Patil, et al., *Hum. Mol. Genet.* 3:1811 (1994) and Chumakov, et al., supra].

Another important application of quantitative DNA fiber mapping is the assessment of the extent of gaps in contig maps. The extent of the gap between clones '1143' and '1107', was determined to be 10.9 μm or 25.4 kb (+/−1.1 kb) by measuring the physical distances between the P1 hybridization signals on 10 YAC fibers. Partial fibers showing hybridization signals along the gap region and part of the flanking P1s were sufficient for determination of the size of the gap region since these all appeared to be equally stretched. FIG. 4C shows the red fluorescence profile determined by averaging 10 individual profiles. The extent of the gap is readily apparent.

c) Triple Color Detection Scheme for the Physical Mapping of P1 Clones on Combed YAC Molecules The construction of high resolution physical maps by quantitative DNA fiber mapping would be expedited by hybridization of several P1 clones labeled with different haptens and detected in different fluorescence wavelength intervals. This example demonstrates the use of a triple color detection scheme for the mapping of P1 clones along a YAC molecule. The P1 clones '1143' and '1107' were labeled with digoxigenin and FITC, respectively, while the YAC '141G6' DNA was biotinylated. Bound probes were detected in red, green and blue, respectively.

i) Labeling of DNA

DNA was isolated from P1 clones '1143' and '1107' as described in section b) above. Labeling of probes with digoxigenin and biotin was performed as described [Weier et al., *Genomics* 24:641 (1994)]. Briefly, clone '1143' was labeled by random priming in the presence of digoxigenin-dUTP as described in Example 2. Clone '1107' was labeled by random priming in the presence of fluorescein-dUTP (BM) as described in Example 2. The biotinylated DNA probe used for counterstaining the YAC '141G6' molecule was generated using biotin-14-dCTP using the BioPrime kit (Gibco-BRL). Digoxigenin-labelled pYAC3 DNA was prepared as described in section b) above.

ii) FISH and Detection of Bound Probes

FISH was performed as described in Example 2 using approximately 20 ng of each of the four labeled DNAs described above. Bound probes containing digoxigenin-labeled probes (i.e., pYAC3 and P1 clone '1143') were detected using a rhodamine-labeled sheep antibody against digoxigenin followed by amplification with a Texas Red-labeled rabbit antibody against sheep IgG as described in Example 2. The biotinylated YAC probe was visualized by incubation with AMCA avidin D (Vector) (blue fluorescence) followed by two signal amplification steps using the biotinylated goat-anti-avidin antibody as described in Example 2. Detection of the FITC-labeled '1107' probe was accomplished using an anti-FITC antibody (raised in mouse; DAKO) followed by incubation with an FITC-conjugated horse-anti-mouse antibody (Vector). Slides were mounted in AF-solution for microscopic analysis.

Figure 5:
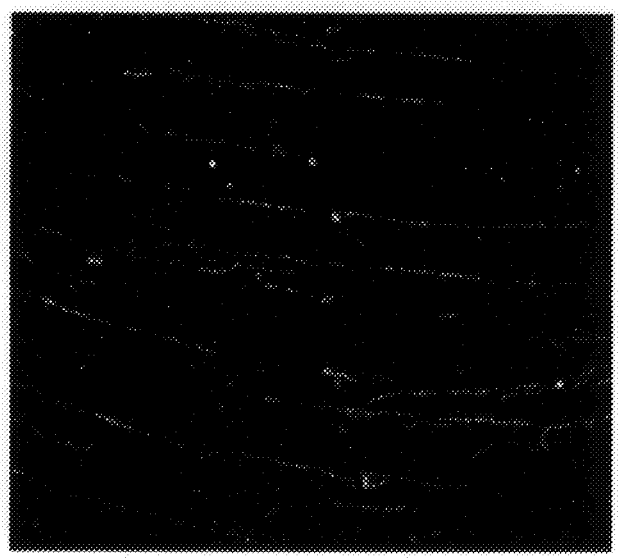
FIG. 5 shows an image (three color) produced by hybridization of stretched '141G6' fibers (YAC clone) with probes corresonding to P1 clone '1143' (red), P1 clone '1107' (green), '141G6' (blue) and pYAC3 (red).

Image analysis was conducted as described in Example 2. Images from the hybridized YAC molecules were recorded using the 40× lens. Representative results are shown in FIG. 5. For the images shown in FIG. 4, contrast enhancement was performed using the high pass filter function (width: 10 pixels) and levels functions of Photoshop 3.0 (Adobe Systems, Inc., Mountain View, Calif.).

In FIG. 5, the blue, red and green fluorescence represents hybridization of the labeled '141G6', '1143' and '1107' probes, respectively. The hybridization mixture also contained digoxigenin-labeled DNA from plasmid pYAC3 (red signals at the ends of the YAC molecules). The image shows a field of view of average DNA fiber density.

FIG. 5 shows an image obtained using the triple color detection scheme and demonstrates the high density of DNA fibers per field of view. The density of fibers shown in FIG. 5 was found to be optimal for analysis. Areas on the slides containing up to a ten time higher density of YAC DNA fibers were also found, but these were more complicated to analyze due to fiber overlap. Fibers selected for analysis were straight molecules showing bead-like hybridization pattern as shown in FIG. 4B for the dual color detection scheme.

The results shown in FIG. 5 demonstrate that quantitative DNA fiber mapping can be performed by hybridization of several P1 clones labeled with different haptens and detected in different fluorescence wavelength intervals. This approach will expedite the construction of high resolution physical maps.

EXAMPLE 4

Mapping of Plasmid DNA Clones to Circular P1 Molecules

While mapping to linear DNA molecules is generally preferred, it is not always easy or possible to linearize every circular clone of interest prior to molecular combing. For this reason the ability to map DNA clones onto circular P1 molecules was investigated.

The cloned probe pADJ762 detects a polymorphism at the locus D11S12 in MspI digested human genomic DNA [Barker, et al. *Am. J Hum. Genetics* 36:1159 (1984)]. One end of pADJ762 was sequenced and oligonucleotides were prepared to permit PCR screening of the Dupont P1 library. A single P1 clone (111H8) was isolated that mapped to the correct chromosome band (11p15.5). This P1 clone presented several problems: DNA yields were unusually low and the isolated DNA could not be digested with NotI, so that PFGE analysis showed mostly circular DNA molecules in the presence of small amounts of linear P1 molecules indicating an unusually small P1 clone of ~55 kb. Furthermore, the vector part of the DNA fibers appeared shorter than usual (~15 kb instead of ~17 kb) suggesting that deletion of the NotI site had occurred.

In order to map the region of overlap between the plasmid probe pADJ762 and 111H8, 111H8 molecules were digested with NotI and linear 111H8 molecules were isolated using PFGE. Molecular combing was conducted and labeled pADJ762 was hybridized to the combed 111H8 fibers using FISH as described above. The results of these experiments showed that the linear 111H8 molecules were randomly sheared DNA molecules (rather than NotI linearized molecules), because the location of the vector sequence was observed randomly along the DNA fibers.

Because NotI linearized 111H8 molecules could not be obtained for mapping, circular 111H8 DNA molecules were isolated from gel slices after PFGE by agarase digestion and the optimized protocol for molecular combing was conducted (Ex. 1). As expected, most circular molecules were not stretched uniformly and most molecules found on the slide were linear (i.e., randomly broken fibers). However, enough circular molecules where observed after FISH to allow mapping of the plasmid probe onto the circular P1 molecule. Probes were labeled and FISH was conducted as follows.

A biotinylated probe was prepared from 111H8 DNA using random priming as described in Example 1. An FITC-labeled probe corresponding to the empty pAD10SacBII P1 vector (~17 kb) was generated by random priming of pAD10SacBII DNA in the presence of fluorescein-dUTP as described in Example 4c. A digoxigenin-labeled PCR product that hybridizes to the P1 vector DNA near the NotI site was generated using the following primer pair in a PCR: F4-P1: 5'-AAAGCT CATCAGCGTGGTCGTG-3' (SEQ ID NO:5) and B5-P1: 5'-TGAGAGCCTTC AACCCAGTCAG-3' (SEQ ID NO:6). Any of the P1 clones can be used as template in the PCR. The approximately 1.4 kb PCR product was precipitated using isopropanol and labeled with digoxigenin-dUTP by random priming. A digoxygenin-labeled DNA probe prepared from plasmid pADJ762 was generated by random priming of pADJ762 DNA in the presence of digoxygenin-dUTP.

Hybridization was conducted using a mixture of all 4 probes (using approximately 20 ng of each probe) and bound probe was detected (triple color detection) as described in Example 4(c)(ii). Representative hybridization results are shown in FIGS. 6A and 6B.

Figure 6:
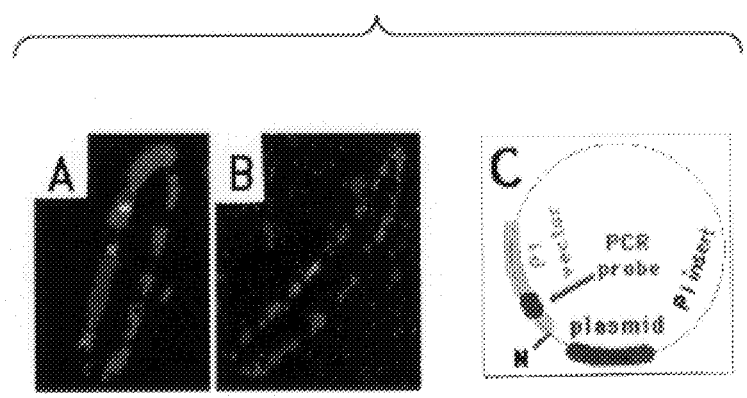
FIG. 6A shows an image (three color) produced by hybridization of stretched circular 111H8 molecules with probes corresponding to pADJ762 (red) pAD10SacBII (green), a PCR product corresponding to a region near the NotI site on pAD10SacBII (red) and 111H8 (blue).
FIG. 6B shows another circular 111H8 molecule following hybridization as described in FIG. 6A.
FIG. 6C provides a schematic map of the hybridized circular 111H8 clones shown in FIGS. 6A and 6B.

In FIG. 6C, a schematic map of the hybridized 111H8 clone is shown. The location of the NotI site present in the normal P1 vector (but absent in the 111H8 clone) is indicated by the "N." The relative locations of the PCR probe to the NotI site is indicated ("PCR probe") and the P1 vector sequences (green) and the insert sequences (blue) is indicated. The location of the region of homology between the insert sequences and the pADJ762 plasmid probe is indicated by the red region labeled "plasmid."

Because the hydrodynamic force did not stretch the circular DNA molecules as well as it does linear molecules, distance measurements were normalized using the known size of the plasmid probe (5.5 kb) as an internal standard. The analysis suggested a distance of 3 kb+/−1.2 kb (N=8) between the T7/NotI end of the vector sequences and the plasmid DNA probe. These results confirmed that the region homologous to pADJ762 is fully contained in P1 clone 111H8.

While not limiting the present invention to any particular theory, the observed binding of circular DNA molecules to APS-derivatized slides may be due to the presence of single strand nicks in the circular DNA molecule. Circular DNA can be purified from plasmid, cosmid, P1, PAC or BAC clones by simple techniques and mapping on to DNA circles would provide savings of both time and costs (e.g., avoid the PFGE steps). In addition to the time savings, the ability to map circular DNA molecules allows one to circumvent problems associated with NotI linearization such as digestion within the insert or, as shown in the case of clone 111H8, loss of the unique NotI site due to deletion of P1 vector DNA.

EXAMPLE 5

Quantitation of the Overlap between Two Linked P1 Clones

In order to demonstrate the utility of the quantitative DNA fiber mapping technique for the determination of the degree of overlap between linked P1 clones, the following experiments were conducted.

Figure 7:
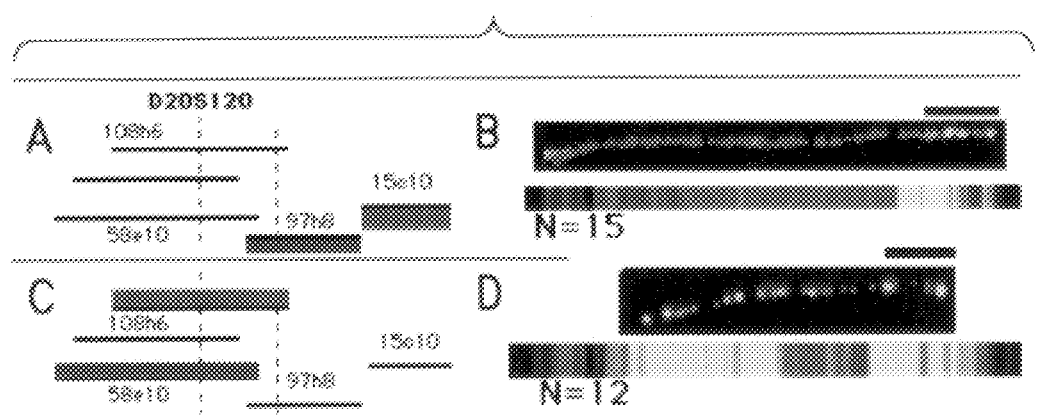
FIG. 7A provides a schematic showing the relative position of P1 clones from the D20S120 marker region as suggested by STS content mapping; red and green boxes are used to indicate the labeling/detection scheme chosen for FISH of selected clones probes to stretched 15c10 fibers.
FIG. 7B shows an image generated by FISH of stretched 15c10 fibers with probes corresponding to 97h8 (red) and 15c10 (green).
FIG. 7C provides a schematic showing the relative position of P1 clones from the D20S120 marker region as suggested by STS content mapping; red and green boxes are used to indicate the labeling/detection scheme chosen for FISH of selected clones probes to stretched 108h6 fibers.
FIG. 7D shows an image generated by FISH of stretched 108h6 fibers with probes corresponding to 58e10 (red) and 108h6 (green).

P1 clones from the D20S120 region, a region located on chromosome 20 (at 20q13) frequently found amplified in human breast cancer have been previously isolated [Tanner, et al., *Cancer Res.* 54:4257 (1994)]. These clones have been mapped by traditional techniques: STS content and EcoRI fingerprinting. FIGS. 7A and 7C show the relative location of the STS marker D20S120 (represented by the left-hand dashed vertical line) and P1 clones 108h, 58e10, 97h8 and 15c10 as suggested by STS content mapping. The red and green boxes are used in FIGS. 7A and 7C to indicate the color scheme employed for detection of these clones by FISH. The overlap between two pairs of P1 clones was examined in this study (pair 1: 108h6 and 58e10; pair 2: 97h8 and 15c10).

Clones 58e10 and 108h6 both contain the STS marker D20S120 [FIGS. 7A (schematic) and 7C (actual FISH image)]. Determination of the end-sequence (T7 end) of the insert of 108h6 generated a new STS (represented as the right-hand dashed vertical line in FIGS. 7A and 7C). This sequence information was used to screen the P1 library by PCR and identified clone 97h8, but this screening did not identify clone 58e10. The clone 15c10 was isolated from the P1 library by hybridization with inter-Alu PCR products from a 1200 kb YAC (820F5) [Cohen, et al. *Nature* 366:698 (1993)] spanning the region surrounding D20S120.

Two different experiments were conducted to analyze the overlap between these P1 clones. In the first experiment, NotI digested PFGE-purified 15c10 molecules were placed on treated slides, combed and probed with digoxigenin-labeled DNA from clone 97h8 [FIGS. 7A (schematic) and 7B (actual FISH image); red] and biotinylated DNA from clone 15c10 [FIGS. 7A (schematic) and 7C (actual FISH image); green]. Preparation of probes, hybridization and detection was performed as described in Example 3b. The analysis of 15 individual molecules showed that there was no overlap between clones 15c10 and 97h8 in the insert region.

In the second experiment, NotI linearized 108h6 molecules were combed and hybridized with digoxigenin-labeled DNA from clone 58e10 [FIGS. 7C (schematic) and 7D (actual FISH image); red] and biotinylated DNA from clone 108h6 [FIGS. 7C (schematic) and 7D (actual FISH image); green]. The clones 108h6 and 58e10 showed significant overlap in the region of the human genomic insert as expected from the earlier STS content mapping. Using quantitative DNA fiber mapping, the region of non-overlap between the clones was determined to be 11 kb+/−2 kb based on the analysis of 12 molecules. The human genomic DNA insert contained within clone 108h6 is ~79 kb+/−1 kb based on PFGE data. Thus, the overlap between clones 108h6 and 58e10 is ~68 kb+/−3 kb.

The above results demonstrate that quantitative DNA fiber mapping can be used to rapidly determine the degree of overlap of linked P1 clones with high resolution.

EXAMPLE 6

High Resolution Mapping of ~3 kb Plasmid Clones (Sequencing Templates)

High density sequence tagged site (STS) maps are required for the rapid walking in large insert genomic DNA libraries and to support sequence assembly. In order to demonstrate the ability of quantitative DNA fiber mapping for the high resolution mapping of sequencing templates, the following experiment was conducted. As a model system, the P1 clone H12 was employed (this clone has not been reported in the literature; it is used here for exemplary purposes only). The insert contained within P1 clone H12 maps to a region on the long arm of chromosome 20 which is amplified frequently in human breast cancer cells [Tanner, et al. *Cancer Res.* 54:4257 (1994)]. Sequencing templates derived from clone H12 were prepared by cloning size selected ~3 kb fragments from sonicated H12 DNA into the plasmid vector pOT 2; pOT 2 is a derivative of pCSOS-4 [Strathman, et al., *Proc. Natl. Acad. Sci. USA* 88:1247 (1991)] which contains the following restriction enzyme sites in the polylinker: XhoI, PvuII, BstXI, XbaI, BamHI, EcoRI, BstXI, EcoRV, and BglII. pOT 2 was designed for use in transposon mapping and sequencing; other suitable plasmid vectors may be substituted for pOT 2.

H12 DNA was isolated using the alkaline lysis protocol (Example 3a) and the extracted DNA was then sonicated to produced fragments having an average size of 3 kb. The sonicated DNA was run on a low melting point agarose gel and fragments of approximately 3 kb in size were excised and the DNA was inserted into the plasmid pOT 2. Eight pOT clones containing fragments of H12 DNA which gave anomalous results upon DNA sequencing were selected for examination by mapping.

Digoxigenin-labeled probes were generated by random priming of plasmid DNA from the 8 sequencing templates (plasmid clones) as described in Example 2. Combed DNA fibers were prepared from NotI-linearized molecules of H12. FISH was carried out as described in Example 4c using hybridization mixtures which contained the desired plasmid probe, 100 ng/μl human Cot-1 DNA (Gibco-BRL) (to block hybridization of DNA repeat sequences), biotinylated H12 DNA (visualized in blue; generated and detected using as described in Example 4c) and an FITC-labeled probe for the P1 vector (green) [generated by random priming of the P1 vector in the presence of fluorescein-dUTP and detected using a mouse anti-FITC antibody followed by an FITC-conjugated horse anti-mouse antibody described in Example 4(c)(ii)]. The bound plasmid DNA was visualized in red. Detection of digoxigenin- and biotinylated-labeled probes was as described in Example 2.

Figure 8:
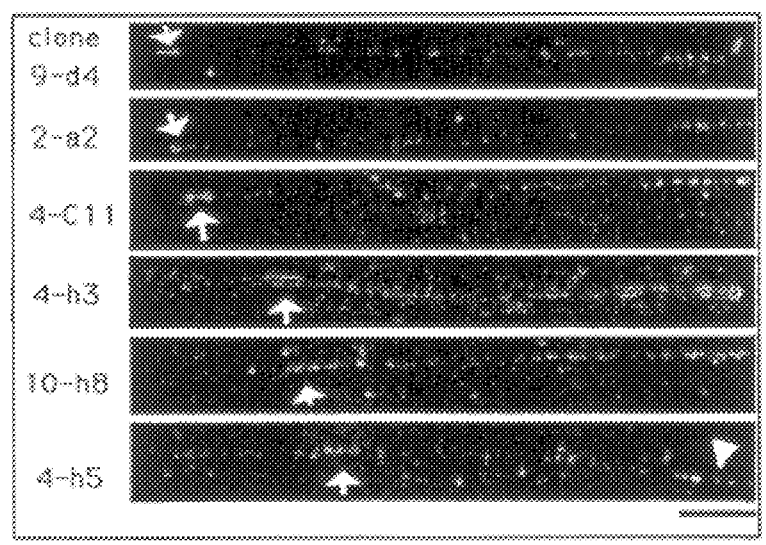
FIG. 8 shows images produced by hybridization of sequencing templates 9-d4, 2-a2. 4-C11, 4-h3, 10-h8 and 4-h5 (top to bottom) to stretched H12 DNA fibers.

Plasmid probes that showed hybridization to vector sequences were also mapped by hybridization to DNA fibers prepared from an empty recombinant P1 (Genome Systems). FIG. 8 shows representative images of hybridized DNA fibers using 6 different plasmid probes (from top to bottom, the following sequencing templates are shown hybridized to P1 clone H12 DNA fibers: 9-d4, 2-a2, 4-Cl1, 4-h3, 10-h8 and 4-h5. The map position of the ~3 kb plasmids was readily visible and is indicated in FIG. 8 by the white arrows. Two hybridization signals were detected when clone 4-h5 was hybridized to H12 fibers; one of these signals was within the insert DNA (arrow) and the other was within the P1 vector sequences (the arrowhead). The horizontal bar represents the part of the DNA fiber representing the P1 vector sequences.

Figure 9:
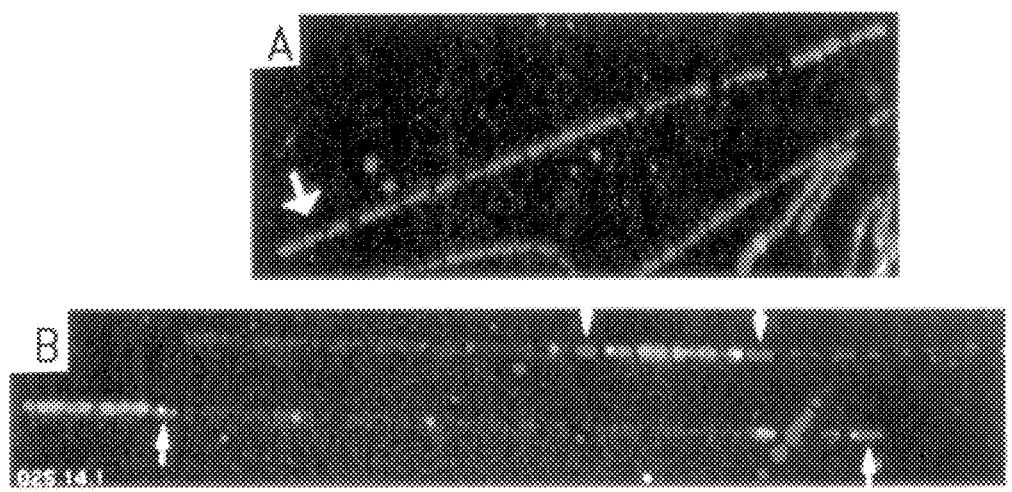
FIG. 9A shows a color reproduction of one of the images (clone 9-d4) shown in black and white in FIG. 7.
FIG. 9B shows a color image produced by hybridization of sequencing templates 1-c7 to stretched H12 DNA fibers.

FIG. 9A provides a color reproduction of one of the images (clone 9-d4) shown in black and white in FIG. 8. In FIGS. 9A and 9B, the green signal represents hybridization of the FITC-labeled probe specific for the P1 vector; the blue signal represents the H12 DNA and the red signal represents hybridization of the ~3 kb sequencing template. Clone 9-d4 showed a single hybridization signal in the insert region approximately 5 kb from the unique NotI site of the P1 vector (FIG. 9A). Clone 1-c7 showed two hybridization domains on either side of the insert (FIG. 9B). The lower molecule shown in FIG. 9B was digested with NotI so that the vector portion (green) is entirely on one end of the fiber. In contrast, the upper DNA molecule shown in FIG. 9B broke randomly within the insert so that vector sequences as well as the plasmid-specific domains appear in the middle of the fiber. Both types of linear molecules (i.e., NotI digested and randomly broken) co-migrated on the pulsed field gel and were purified from the band containing linear DNA molecules.

The map positions of the sequencing templates were measured relative to the SalI (Sp6) site of the P1 vector pAD10SacBII. Clones 1-h3, 9-d4, 2-a2, 4-cl 1, 4-h3 and 10-h8 were found to map exclusively to the insert of H12, while clones 1-c7 and 4-h5 hybridized to insert as well as vector regions. Gel electrophoretic analysis indicated that clones 1-c7 and 4-h5 were significantly larger than the other clones (see Table 1 below). Clone 1-c7 mapped to the insert adjacent to the unique NotI (T7) site at approximately the same position as clone 1-h3, but showed an additional hybridization signal adjacent to the SalI site (FIG. 9B). Clone 4-h5 hybridized to the insert approximately 52±4 kb from the SalI site, and showed a second hybridization signal of approximately 3 kb centered between positions 4500 and 7500 of the 16 kb pAD10SacBII vector (Genbank accession #U09128) as shown in FIG. 10.

Figure 10:
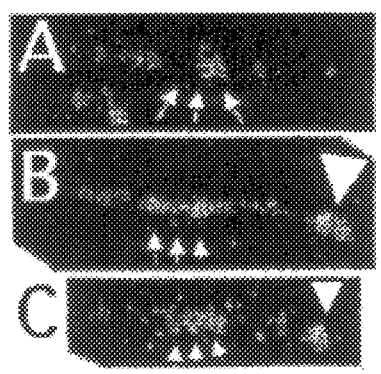
FIG. 10A shows an enlargement of the image shown in FIG. 8 (clone 4-h5).
FIGS. 10B and C show the images produced from the hybridization of a plasmid probe to the empty pAD10SacBII vector.

In FIG. 10, the triple arrows indicate the (red) hybridization signal in the (green) part of the P1 vector. Panel A is an enlargement of part of the image shown in FIG. 8 (clone 4-h5). The images shown in FIG. 10, Panels B and C depict the results from hybridization of the plasmid probe to recombinant (empty) pAD10SacBII. The arrowhead points to the red signal generated from a ~1400 bp PCR probe that was included to indicated the orientation of the P1 vector molecule.

TABLE I

Mapping ~3 kb Sequencing Templates on P1 DNA Fibers

| clone ID | proximal position (kb) | distal position (kb) | plasmid insert size (kb)[1] | homology with vector | vector map position |
|---|---|---|---|---|---|
| 1-h3 | 80 ± 1.6 | 83 ± 1.3 | 2.6 | No | — |
| 9-d4 | 77.3 ± 1.4 | 79.6 ± 1.3 | 2.9 | No | — |
| 2-a2 | 76.3 ± 1.3 | 79.5 ± 1.3 | 3.2 | No | — |
| 4-c11 | 74 ± 2.2 | 77.5 ± 1.9 | 3.4 | No | — |
| 10-h8 | 55.1 ± 1.7 | 58.8 ± 1.9 | 3.6 | No | — |
| 4-h3 | 54.3 ± 3.2 | 58.8 ± 3.2 | 4.5 | No | — |
| 4-h5 | 52.3 ± 3.8 | 56.4 ± 4.2 | 6.4 {2.3, 4.1} | Yes | 4560–7500 |
| 1-c7 signal1 | 0 | 3.4 ± 0.6 | 8.0 kb | Yes | SalI side |
| 1-c7 signal2 | 82.8 ± 4.1 | 85.1 ± 4.2 | | Yes | NotI side |

[1]Measured by agarose gel electrophoresis.

The above results demonstrate that quantitative DNA fiber mapping can localize ~3 kb sequencing templates on P1 molecules with a precision of a few kb, identify chimeric clones and clones that contain vector sequences. Simultaneous hybridization of 2 clones using the triple color scheme described in Example 4c would allow the overlap or distance between clones to be determined with even higher precision due to direct visualization of overlapping regions and measurement of shorter distances.

EXAMPLE 7

Mapping of Alu-Type Repeat Clusters in Linearized P1 DNA Molecules

Mapping of the cosmid clone pBHp53-2 to the P1 clone RMC17P036 by FISH showed weak hybridization signals located at definite locations along the P1 fiber DNA in addition to the strong hybridization seen which corresponded to hybridization of the entire cosmid along the P1 fiber (Example 3a). The weaker hybridization signals were shown to be due to the presence of Alu repeats found in both the cosmid probe and the P1 clone. In this experiment, the localization of Alu repeats along the RMC17P036 molecule is further investigated by hybridization of a cloned Alu repeat probe.

A cloned Alu repeat probe was used to generate a digoxigenin-labeled probe as follows. The DNA insert in the Alu repeat probe PV72 (Genbank accession number M33776;Matera, et al., supra) was amplified by PCR using the vector specific primers M13F: 5'-GTAAAACGACGGCCAGT-3' (SEQ ID NO:7) and M13R: 5'-AACAGCTATGACCATG-3' (SEQ ID NO:8). The PCR products were precipitated using isopropanol and labeled with digoxigenin-dUTP by random priming.

Figure 11:
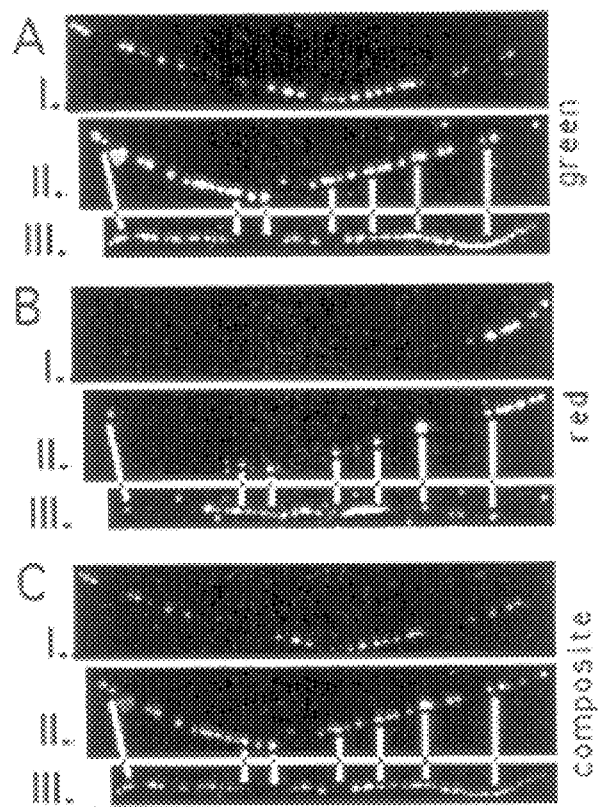
FIG. 11A shows the green fluorescence produced from hybridization of three probes to RMC17P036 DNA fibers.
FIG. 11B shows the red fluorescence produced from hybridization of three probes to RMC17P036 DNA fibers.
FIG. 11C shows the composite (red/green/blue) fluorescence produced from hybridization of three probes to RMC17P036 DNA fibers.

P1 RMC17P036 fibers were combed as described in Ex. 3a. Hybridization of the RMC17P036 fibers was carried out using combinations of biotinylated RMC17P036 DNA (a, green), digoxigenin-labeled recombinant P1 vector (b, red) (prepared by random priming of the empty P1 vector in the presence of digoxigenin-dUTP), digoxigenin-labelled Alu repeat probe (c, red) and digoxigenin-labelled pBH53-2 DNA (d, red). The results are shown in FIG. 11, Panels A–C. In FIG. 11, hybridization mixtures I–III contained probes a and b, a, b, and c and a and d, respectively. Red, green and composite (i.e., red/green/blue) images of representative molecules are shown in FIG. 11, Panels A, B and C, respectively. The "green" images delineate P1 clone RMC17P036 molecules that were deposited on the slides. The "red" images show regions of homology such as between the P1 vector sequences in hybridization mixtures I and II, Alu repeats in II or human genomic DNA cloned in cosmid pBHp53-2 DNA in III. In the composite images, the Alu repeat clusters appear as yellow dots in II and III due to superposition of the green P1 probe with red Alu repeat signals from the clonal repeat DNA or the cosmid probe. Vertical lines indicate the approximate position of the Alu repeat clusters.

As shown in FIG. 11, hybridization of the Alu probe PV72 to linearized high molecular weight P1 DNA molecules from clone RMC17P036 containing the human p53 gene showed specific pattern and qualitative co-localization of Alu-specific and cosmid pBHp53-2 hybridization signals along the non-homologous part of RMC17P036.

The results shown in FIG. 11 demonstrates the use of quantitative DNA fiber mapping for the physical mapping of DNA repeat clusters. These results also show the application of a vector specific DNA probe to allow for the specific delineation of the cloning vector portion of the P1 molecule (by the hybridization of the randomly primed recombinant pAD10SacBII P1 vector). The use of vector specific probes provides a means to ascertain whether the combed DNA fiber is truncated (at the end of the fiber containing sequences complementary to the vector-specific probe). The use of vector-specific provides also permits the orientation of the DNA insert to be rapidly determined [using the pAD10SacBII vector as an example, after digestion with NotI the insert will be located next to the unique SalI site (or Sp6 promoter) in the vector]. Vector-specific probes provide a control for the hybridization efficiency between experiments (the signal is expected to be of approximately the same intensity in all experiments thereby providing a convenient means of quality control). Thus, the use of vector-specific probes in the methods of the present invention overcome deficiencies in existing mapping methods. Furthermore, vector-specific probes can be used to provide an internal standard for normalization when mapping is conducted on molecules which are not completely stretched (e.g., when circular DNA molecules are utilized).

EXAMPLE 8

DNA Fiber Microdissection

The quantitative DNA fiber mapping technique allows the microdissection of DNA fibers. In theory, microdissection of DNA fibers is very similar to chromosome microdissection which has been applied for generation of chromosome band specific DNA libraries [Luedecke, (1989); Luedecke, (1990); and Meltzer, (1992)]. Genomic DNA from the target region of the genome is mechanically isolated using a fine tip glass capillary and subjected to PCR amplification. However, in practice important differences exist between the microdissection of chromosomal DNA and DNA fibers. In particular, the dissection of DNA fibers, unlike the dissection of metaphase chromosomes, provides extremely small quantities of DNA (a few molecules of several hundred bp each), and high efficiency of subsequent amplification is crucial for successful cloning and sequencing of DNA removed from the fibers.

In order to promote high efficiency of the amplification of DNA removed from DNA fibers, PCR-amplified DNA is bound to the target region prior to microdissection. Probes were prepared using 3'-mixed base primers harboring non-homologous 5'-sequences (DOP-PCR) [Telenius, et al., Genes, Chromosomes and Cancer 4:257 (1992) and Weier, et al., DNA Sequence 4:47 (1993)]. Such probe molecules carry binding sites for PCR primers, so that they can be amplified with high efficiency, while genomic DNA might not be amplified at all [Carter, Cytometry 18:2 (1994)].

Probe DNA was prepared from PFGE-purified DNA of clone '141G6' by a 40 cycle DOP-PCR using primer JUN1 (5'-CCCAAGCTTGCATGCGAATTCN NNNCAGG-3'; where N=ACGT) (SEQ ID NO:9) [Weier, et al., DNA Sequence 4:47 (1993)] with an initial 8 cycles of primer annealing at 37° C. and extension by T7 DNA polymerase [Kroisel, 1994 #975]. This oligonucleotide primes amplification from genomic templates only when annealed at low temperature (30°–40° C.), while the PCR products can be further amplified at higher annealing temperature (50°–55° C.) using primer JUN1 (SEQ ID NO:9) or JUN15 (5'-CCCAAGCTTGCATGCGAATTC-3'; SEQ ID NO:10). The probe was labeled by incorporation of biotin-dUTP using an aliquot from the above PCR as follows. Two microliters from the first PCR were resuspended in 50 μl of biotinylation PCR buffer containing 1 unit AmpliTaq (Perkin Elmer). The biotinylation PCR buffer contains 100% biotin-dUTP instead of dTTP in the standard PCR buffer described in Example 3 [Weier, et al., J. Histochem. Cytochem. 38:421 (1990)]. Twenty-five additional cycles of amplification were conducted which comprised: ramp to 92° C. over 30 sec; hold at 92° C. for 1 min; ramp to 55° C. over 1 min; hold at 55° C. for 1 min; ramp to 72° C. over 2; hold at 72° C. for 3 min.

In situ suppression hybridization to human metaphase spreads [Trautmann, et al., Hum. Genet. 87:495 (1991)] confirmed binding of this PCR probe exclusively to the target region on the long arm of chromosome 21.

Figure 12:
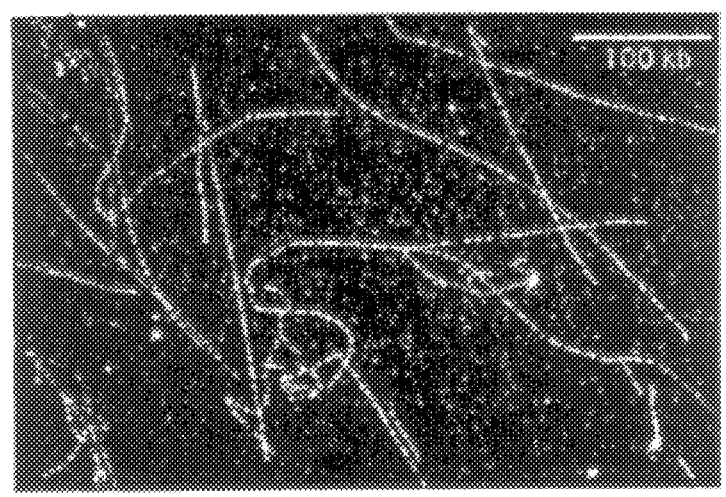
FIG. 12 shows an image produced by FISH of a DOP-PCR probe to stretched '141G6' DNA fibers.

Hybridization of stretched DNA fibers from YAC clone '141G6' with the DOP-PCR probe demonstrated high complexity of the probe and homogeneous labeling along the DNA fibers (FIG. 12). The hybridization of the DOP-PCR probe was carried out using 1 μl (approximately 20–40 ng) of biotinylated DOP-PCR product (prepared as described above). As shown in FIG. 12, incubation with avidin-FITC after hybridization showed homogeneous labeling of the DNA fibers. In FIG. 12, the size marker bar represents 100 kb.

Stretched fibers of '141G6' DNA were prepared using APS-treated glass (borosilicate) coverslips (prepared as described in Example 1 with the exception that coverslips were used in place of slides). The stretched '141G6' DNA fibers were hybridized simultaneously with the biotinylated DOP-PCR probe and digoxigenin-labeled probes from P1 clones '1107' and '1143' (prepared as described in Example 3b) so that the gap region and the P1 hybridization domains appeared green and red, respectively, after incubation with avidin-FITC and anti-digoxigenin rhodamine and one round of signal amplification (see, FIG. 2B for a representative image).

Using an inverted microscope, DNA probes which bound in the gap region were removed using glass microcapillaries prepared for chromosome microdissection. On the inverted fluorescence microscope, the gap (green) as well as the flanking regions (red) were clearly visible by eye. On most coverslips, the probe molecules could not be dislocated from the target region by repeated scratching with the capillary over the target suggesting tight binding of these relative small molecules to the glass surface. In a few experiments, it seemed that the capillary scratched the DNA fiber and moved probe molecules away from the target region. All experiments were performed in air on dehydrated preparations, and were complicated by rapid fading of the fluorescence signals. Capillaries were changed after each experiment. The tips of three capillaries used in the experiments were then immersed (separately; 1 tip/PCR) in 50 μl of a solution comprising 1× PCR buffer (BM), 200 nM all four dNTPs, 2 units/100 μl AmpliTaq (Perkin-Elmer) and 1 μl of a 30 μM solution of primer JUN15. Forty cycles of PCR were carried out as follows. Ramp to 92° C. over 30 sec; hold at 92° C. for 1 min; ramp to 55° C. over 30 sec; hold at 55° C. for 1 min; ramp to 72° C. over 30 sec; hold at 72° C. for 3 min.

Gel electrophoretic analysis of 5 μl aliquots after 40 PCR cycles showed no amplification products. One tenth of each initial PCR was then resuspended in fresh PCR buffer (50 μl) and subjected to another 25 PCR cycles. One of the three PCRs showed specific amplification of a ~500 bp product.

This 500 bp PCR product is purified by electrophoresis on a LMP agarose gel and the DNA is extracted from the gel by agarase digestion as described in Example 1. The isolated DNA is precipitated with ethanol in the presence of 1 μg of glycogen to ensure complete precipitation. The purified PCR fragment is then cloned into pCRII using a TA Cloning kit (Invitrogen); this kit allows the direct cloning of PCR products without modification or restriction of the PCR product [If low cloning efficiencies are obtained using the TA Cloning kit (Invitrogen), other approaches known to the art such as the use of the CloneAmp System (Gibco-BRL) which employs uracil DNA glycosylase or the pCR-Script SK(+) Cloning kit (Stratagene) may be utilized]. Transformants containing plasmids with the PCR product as an insert are then plated on appropriate selective medium and individual clones are selected for analysis. Small scale preparations of plasmid DNA are generated from each individual clone using standard techniques, the DNA is precipitated and resuspended in TE buffer (pH 7.4–8.0) or water. An aliquot is subjected to PCR analysis using the JUN15 primer (SEQ ID NO:10) as described above. Clones producing a 500 bp PCR product are selected for further analysis.

DNA from clones containing an insert which produces the expected 500 bp PCR product is labeled produce a probe for FISH in conjunction with the stretched '141G6' YAC fiber. FISH is performed using the triple color detection scheme (Example 4c). The YAC clone '141G6' is labeled with biotin and detected with avidin-AMCA (blue). The two flanking P1 clones '1107' and '1143' are labeled with digoxigenin and detected with a rhodamine-labeled anti-digoxigenin antibody. The 500 bp PCR product is labeled with FITC (green). Labeling of probes is performed by random priming, hybridization and detection of labeled probes and image analysis is conducted as described in the previous examples.

PCR products which map into the gap region are detected by the presence of green fluorescence between the two flanking P1 probes which appear as red fluorescence. PCR products which map to the gap region are then subjected to DNA sequencing using standard techniques (numerous companies provide DNA sequencing services, for example, US Biochemicals). The determination of the DNA sequence of the PCR product provides both a functional probe and sequence information for this region of the genome. The PCR product can be used to screen large insert libraries (cosmid, PAC, P1) to isolate clones which close the gap present between P1 clones '1107' and '1143'. Quantitative DNA fiber mapping is used to confirm that the isolated clones do indeed close the gap as follows. FISH is conducted using stretched '141G6' YAC fibers. The P1 clones known to flank the gap (i.e., '1107' and '1143') are labeled to produce red fluorescence; the newly identified clone is labeled with FITC (green) and the '141G6' YAC DNA is labeled to produce blue fluorescence. If the gap is closed, the gap region will appear green-blue and regions of yellow color will be produced due to overlap between the newly isolated, gap-filling clone (green) and the two flanking P1 clones (red).

EXAMPLE 9

Comparative Genomic Hybridization Using Combed DNA Fibers

Comparative genomic hybridization (CGH) is a diagnostic procedure which allows the comparison of the relative number of DNA segments in two pools of DNA [Kallioniemi, et al., *Science* 258:818 (1992)]. CGH has been applied for the detection of genetic changes (e.g., amplifications and deletions) in tumor DNA samples by comparing genomic DNA from derived a tumor specimen with genomic DNA derived from normal individuals. As traditionally practiced, CGH involves the simultaneous hybridization of differentially labeled tumor (or test) DNA and normal (or reference) DNA to normal metaphase chromosome spreads. The two probe pools (i.e., the labeled tumor and normal DNA samples) will compete for binding to the complementary DNA hybridization targets on metaphase chromosomes. The probe pool that contains more copies of a particular DNA segment will be present at a higher relative concentration in the probe mixture than in the other DNA pool and may therefore bind more of its probe molecules to the target sequences. DNA segments contained in both probes at equal concentration are expected to bind in a 50:50 ratio. Unlabelled highly repetitive DNA (COT-1 DNA, Gibco-BRL) is included in the hybridization mixture to suppress hybridization of repetitive DNA which may be subject to heteromorphisms or which does not bind in a region-specific manner. The amount of bound probe along individual chromosomes is detected after hybridization by fluorescence microscopy and image analysis.

When the tumor DNA is labelled with a fluorochrome that produces green fluorescence and the normal DNA is labelled with a fluorochrome which produces red fluorescence, regions that are amplified in tumor appear relatively stronger in green (relatively in comparison to regions of normal copy number), and regions that are deleted in tumors appear relatively stronger in red along the length of the target sequences (e.g., metaphase chromosomes).

When practiced on metaphase chromosomes, the resolution of CGH for the detection of deletions in the tumor genome is about 10 Mb. Similarly, genomic regions which are amplified in the tumor must be either large in size or present in many copies in order to be detectable by fluorescence microscopy. For example, if the degree of amplification is low, the size of the amplified region (i.e., the amplicon) must be about 0.5 to 10 Mbp to permit detection using metaphase chromosomes. When the degree of amplification is higher (16–24 copies or more), amplicons having a size of about 200–300 kb are detectable using metaphase chromosomes. In any case, the highly condensed DNA of metaphase chromosomes severely limits the resolution with which an amplified or deleted region can be mapped.

The technique of DNA fiber mapping described herein can be used to overcome some of the above limitations of CGH by performing the competitive hybridization on DNA fibers. This will limit the region under investigation the size of the DNA molecule, but allow the resolution of deletions and/or amplified regions to within a few kb.

a) Detection of Deletions

Deletions of genes including tumor suppressor genes (e.g., the human p53 gene) is known to occur in tumors. In order to determine whether a particular gene or chromosomal region is deleted in a tumor sample, DNA from a YAC or other large insert DNA clone that spans the region of interest is stretched onto an APS-derivatized slide or coverslip as described in Example 1. CGH using stretched DNA fibers will allow the localization of the deletion with high resolution. This is desirable when for instance several genes are located within the area of interest and therefore the extent of the deletion present must be ascertained precisely so that it may be determined whether the gene of interest is deleted.

Genomic DNA is extracted from tumor cells (the tumor cells may be derived from a cultured cell line, a portion of a solid tumor, blood, etc.) and from normal human cells using standard techniques [Sambrook et al., *Molecular Cloning: A Laboratory Manual*, Cold Spring Harbor Press, Cold Spring Harbor, pp. 9.16–9.23 (1989)]. The tumor DNA is labeled with digoxigenin (red fluorescence produced by detection with a rhodamine-labeled anti-digoxigenin antibody) by nick translation using a BioNick Labelling System kit (Gibco-BRL) in the presence of digoxigenin-11-dUTP. The normal DNA is labeled with biotin (green fluorescence produced by detection with avidin-FITC) by nick translation using a BioNick Labelling System kit (Gibco-BRL) in the presence of biotin-14-dATP. Suitable probes may also be generated by labeling the probe DNA directly with fluorochromes (i.e, the use of fluorescein-dUTP or rhodamine-dUTP); direct fluorescenation of the probe obviates the need for secondary detection of the labeled DNA.

Approximately equal amounts of both probes are mixed with an excess of unlabeled Cot1 DNA and applied to DNA fibers prepared from the large insert DNA clone. Hybridization probes are applied using 400–4000 ng of each probe; 1–40 μg of blocking DNA (Cot-1, Gibco-BRL) is employed and hybridization is conducted at 37° C. in a humidified chamber as described in Example 2 with the exception that hybridization is allowed to proceed for 2–4 days. Detection of hybridized probes and image analysis is performed as described above (Examples 2–7).

The presence of the bound probes is detected directly or by immunocytochemical detection as described in Examples 2–7 (e.g., avidin-FITC and rhodamine-labeled anti-digoxigenin antibodies are used when the probes are labeled with biotin and digoxigenin). Following image analysis, the regions present in an equal number of copies (i.e., two copies for autosomal sequences) will have bound equal amounts of the red and green probes and will therefore appear in mixed color (yellow). Regions which are deleted in the tumor will have bound mostly "normal DNA" probe (this depends whether one or both copies are deleted in the tumor) and will therefore appear in red. Mapping of the extend of deletion at kb resolution is achieved by measuring the ratio of red-to-green fluorescence along the DNA molecules.

b) Detection of Gene Amplification

Amplification of genes is known to occur in tumors; in particular, a number of oncogenes have been found to be amplified in a variety of tumors. For example, the myc gene has been found to be amplified in colorectal, breast and neuroblastoma tumor lines while the erbB2 gene has been found to be amplified in breast and small cell lung tumor lines. These amplification events can be detected using DNA fiber mapping using the same approach described above for the detection of deletions. Gene amplification in tumors will result in a relative higher number of copies of this region in the tumor genomic DNA as compared to normal DNA. The opposite result, compared to the detection of deletions using CGH and DNA fibers (in terms of fluorescence readout), is obtained when an amplification is present: regions of amplification appear relatively stronger in green fluorescence and less red fluorescence is seen while non-amplified regions appear in yellow.

Target DNA (YACs or other large insert clones) is stretched and tumor and normal DNA probes are labeled as described above. After hybridization as described above, genomic regions amplified in the tumor are expected to have bound a higher amount of green probe compared non-amplified regions. Using the image analysis tools described in Example 1, green-to-red profiles along the hybridized DNA molecules are determined. The green-to-red profile will be approximately 1.0 for regions of normal copy number; greater than 1.0 for regions containing amplifications and less than 1.0 for regions containing deletions.

We claim:

1. A method of treating a nucleic acid fiber immobilized to a solid support comprising:

a) providing:
        i) a stretched nucleic acid fiber having a sequence immobilized to a solid support; and
        ii) one or more labeled probes containing sequences essentially complementary to said sequence of said immobilized nucleic acid fiber;
    b) reacting said immobilized nucleic acid fiber with said probes under conditions wherein said probes are capable of binding to essentially complementary sequences present on said nucleic acid fiber and wherein no substantial background is produced; and
    c) detecting the presence of probes bound to said nucleic acid fiber.

2. The method of claim 1 wherein said nucleic acid fiber is double-stranded.

3. The method of claim 1 wherein said nucleic acid fiber is single-stranded.

4. The method of claim 1 wherein said nucleic acid fiber is a deoxyribonucleic acid fiber.

5. The method of claim 1 wherein said nucleic acid fiber is a ribonucleic acid fiber.

6. The method of claim 1 wherein said nucleic acid fiber is uniformly stretched to a dimension of approximately 2.3 kilobases per micrometer.

7. The method of claim 1 wherein said solid support comprises a glass support treated with 3-aminopropyltriethoxysilane.

8. The method of claim 1 wherein said labeled probe comprises a probe containing a reporter molecule selected from the group consisting of biotin and digoxigenin.

9. The method of claim 8 wherein the detection of step c) comprises reacting said probe bound to said nucleic acid fiber with a detection reagent selected from the group consisting of AMCA-avidin, FITC-avidin, and rhodamine-labeled anti-digoxigenin antibodies.

10. The method of claim 1 wherein said labeled probe comprises a probe containing a reporter molecule selected from the group consisting of rhodamine and fluorescein isothiocyanate.

11. A method for the stretching of a nucleic acid molecule, comprising:

a) providing:
        i) a first solid support treated with 3-aminopropyltriethoxysilane;
        ii) a solution comprising a nucleic acid molecule; and
        iii) a second solid support; and
    b) placing an aliquot of said solution comprising said nucleic acid molecule onto said first solid support;
    c) placing said second solid support on top of said aliquot of said solution to cover said solution; and
    d) allowing said solution to dry whereby said nucleic acid molecule is uniformly stretched to a dimension of approximately 2.3 kilobases per micrometer.

12. The method of claim 11 wherein said nucleic acid molecule comprises a linear nucleic acid molecule.

13. The method of claim 11 wherein said target nucleic acid molecule comprises a circular nucleic acid molecule.

* * * * *